(12) United States Patent
Arendash et al.

(10) Patent No.: US 10,149,982 B2
(45) Date of Patent: *Dec. 11, 2018

(54) PREVENTION AND TREATMENT OF BRAIN DISEASES AND DISORDERS RELATED TO ABNORMAL PROTEIN AGGREGATION THROUGH ELECTROMAGNETIC FIELD TREATMENT

(71) Applicants: Gary W. Arendash, Prescott, AZ (US); Chuanhai Cao, Temple Terrace, FL (US); Jun Tan, Tampa, FL (US)

(72) Inventors: Gary W. Arendash, Prescott, AZ (US); Chuanhai Cao, Temple Terrace, FL (US); Jun Tan, Tampa, FL (US)

(73) Assignees: University of South Florida, Tampa, FL (US); The United States of America as represented by the Department of Veterans Affairs, Washington, DC (US)

( * ) Notice: Subject to any disclaimer, the term of this patent is extended or adjusted under 35 U.S.C. 154(b) by 215 days.

This patent is subject to a terminal disclaimer.

(21) Appl. No.: 14/976,986

(22) Filed: Dec. 21, 2015

(65) Prior Publication Data

US 2016/0106997 A1 Apr. 21, 2016

Related U.S. Application Data

(63) Continuation-in-part of application No. 13/230,415, filed on Sep. 12, 2011, now Pat. No. 9,238,149, which (Continued)

(51) Int. Cl.
*A61N 2/00* (2006.01)
*A61N 5/02* (2006.01)
*A61N 2/02* (2006.01)

(52) U.S. Cl.
CPC ............... *A61N 2/006* (2013.01); *A61N 5/02* (2013.01); *A61N 2/02* (2013.01)

(58) Field of Classification Search
CPC ............. A61N 2/006; A61N 2/02; A61N 5/02
See application file for complete search history.

(56) References Cited

U.S. PATENT DOCUMENTS 4,813,399 A 3/1989 Gordon
4,913,153 A * 4/1990 Hagmann ................ A61B 5/05
324/127

(Continued)

FOREIGN PATENT DOCUMENTS

EP 1 907 052 B1 1/2010
EP 1 364 182 B1 1/2012

(Continued)

OTHER PUBLICATIONS

Scholtzova et al. "Memantine Leads to Behavioral Improvement and Amyloid Reduction in Alzheimer's-Disease-Model Transgenic Mice Shown as by Micromagnetic Resonance Imaging", J Neurosci Res. Sep. 2008; 86(12): 2784-2791.*

(Continued)

*Primary Examiner* — Kaylee R Wilson
(74) *Attorney, Agent, or Firm* — Molly L. Sauter; Nilay J. Choksi; Smith & Hopen, P.A.

(57) ABSTRACT

A method of treating and preventing a neurological disorder, such as Alzheimer's disease, in a subject in need thereof by positioning an electromagnetic field emitting source proximal to the subject and exposing the subject to an electromagnetic field having a predetermined frequency (preferably ≈300-3,000 MHz) for a predetermined absorption period (preferably greater than ≈3 days). Each individual treatment (comprising exposure to the predetermined frequency for the predetermined absorption period) is continued at a predetermined schedule for a predetermined treat- (Continued)

ment period. The EMF can have a specific absorption rate up to about 8 W/kg. The methodology enhances cognition in the subject and/or treats/prevents the underlying neurological disorder or a symptom thereof.

27 Claims, 13 Drawing Sheets

Related U.S. Application Data is a continuation of application No. PCT/US2010/026952, filed on Mar. 11, 2010.

(60) Provisional application No. 61/159,251, filed on Mar. 11, 2009.

(56) References Cited

U.S. PATENT DOCUMENTS

| | | | |
|---|---|---|---|
| 4,923,437 A | 5/1990 | Gordon | |
| 5,752,911 A | 5/1998 | Canedo et al. | |
| 5,885,976 A | 3/1999 | Sandyk | |
| 7,333,859 B2 | 2/2008 | Rinaldi et al. | |
| 7,389,179 B2 | 6/2008 | Jin et al. | |
| 7,551,957 B2 | 6/2009 | Whelan et al. | |
| 7,949,401 B2 | 5/2011 | Fowler et al. | |
| 2003/0055471 A1* | 3/2003 | Fenn | A61N 5/02 607/101 |
| 2003/0171640 A1 | 9/2003 | Canedo | |
| 2006/0135574 A1 | 6/2006 | Day et al. | |
| 2006/0217781 A1 | 9/2006 | John | |
| 2006/0241333 A1 | 10/2006 | Hunter | |
| 2007/0078292 A1 | 4/2007 | Markov et al. | |
| 2007/0282388 A1 | 12/2007 | Sandyk | |
| 2008/0039895 A1 | 2/2008 | Fowler et al. | |
| 2009/0125091 A1* | 5/2009 | Schoenbach | A61N 1/40 607/156 |
| 2009/0276019 A1 | 11/2009 | Perez et al. | |
| 2009/0326315 A1 | 12/2009 | Nishi et al. | |
| 2011/0118534 A1 | 5/2011 | Baror et al. | |
| 2012/0089201 A1 | 4/2012 | Pilla | |

FOREIGN PATENT DOCUMENTS

| | | | |
|---|---|---|---|
| EP | 1 606 010 B1 | 2/2012 | |
| WO | 2004080531 A2 | 9/2004 | |
| WO | 2007044386 A2 | 4/2007 | |
| WO | 2007090054 A2 | 8/2007 | |
| WO | 2007121133 A2 | 10/2007 | |
| WO | 2008141296 A1 | 11/2008 | |
| WO | WO 2009013630 A2 * | 1/2009 | A61K 41/0052 |

OTHER PUBLICATIONS

Shallom et al. "Microwave Exposure Induces Hsp70 and Confers Protection Against Hypoxia in Chick Embryos", Journal of Cellular Biochemistry, 86: 490-496 (2002).*
Brown "Heat Shock Proteins and Protection of the Nervous System", Ann. N.Y. Acad. Sci., 1113: 147-158 (2007).*
Sandyk. 1992. "Magnetic Fields in the Therapy of Parkionsonism." Intern. J. Neuroscience. vol. 66. pp. 209-235.
Kemal Irmak et al. Effects of Electromagnetic Radiation from a Cellular Telephone on the Oxidant and Antioxidant Levels in Rabbits. Cell Biochem. and Function vol. 20. pp. 279-283. (2002).
Sienkiewicz et al. Low-Level Exposure to Pulsed 900 MHz Microwave Radiation Does not Cause Deficits in the Performance of a Spatial Learning Task in Mice. Bioelectromagnetics. vol. 21. pp. 151-158. (2000).
Dubreuil et al. Head-Only Exposure to GSM 900-MHz Electromagnetic Fields Does Not Alter Rat's Memory in Spatial and Non-Spatial Tasks. Behav. Brain Res. vol. 145. pp. 51-61. (2003).
Kwon et al. Effects of Mobile Phone Electromagnetic Fields: Critical Evaluation of Behavioral and Neurophysiological Studies. Bioelectromagnetics. vol. 32. pp. 253-272. (2011).
Arendash et al. A Diet High in Omega-3 Fatty Acids Does Not Improve or Protect Cognitive Performance in Alzheimer's Transgenic Mice. Neuroscience. vol. 149. pp. 286-302. (2007).
Cardozo-Pelaez et al. DNA Damage, Repair, and Antioxidant systems in Brain Regions: A Correlative Study. Free Rad. Biol. Med. vol. 28. pp. 779-785. (2000).
Levine et al. Determination of Carbonyl Content in Oxidatively Modified Proteins. Meth. Enzymol. vol. 186. pp. 464-478. (1990).
Sandyk. Alzheimer's Disease: Improvement of Visual Memory and Visuoconstructive Performance by Treatment with Picotesla Range Magnetic Fields. Int J Neurosci. vol. 76. pp. 185-225. (1994).
Brody et al. Amyloid-Beta Dynamics Correlate with Neurological Status in the Injured Human Brain. Science. vol. 321. pp. 1221-1224. (2008).
Boggio et al. Temporal Cortex DC Stimulation Enhances Performance on a Visual Recognition Memory Task in Alzheimer's Disease. J. Neurol. Neurosurg. Psychiatry. doi:10.1136/jnnp.2007.141853 (2008).
Chang I.F., Hsiao H.Y., Induction of RhoGAP and pathological changes characteristic of Alzheimer's disease by UAHFEMF discharge in rat brain. Curr Alzheimer Res. Dec. 2005; vol. 2, Issue 5, 559-569.
John B. Asbury, et al., Hydrogen bond breaking probed with multidimensional stimulated vibrational echo correlation spectroscopy. J. Chem. Phys., vol. 119, No. 24, Dec. 22, 2003, pp. 12981-12997.
Marcelo J. Kogan, et al., Nanoparticle-Mediated Local and Remote Manipulation of Protein Aggregation. NANO Letters, vol. 6, No. 1, (2006) pp. 110-115.
Haarala et al., 902 MHz Mobile Phone Does not Affect Short Term Memory in Humans. Bioelectromagnetics. 2004. vol. 25: 452-456.
Besset et al., No Effect on Cognitive Function From Daily Mobile Phone Use. Bioelectromagnetics. 2005. vol. 26:102-108.
Russo et al., Does Acute Exposure to Mobile Phones Affect Human Attention?. Bioelectromagnetics. 2006. vol. 27: 215-220.
Ratcliff et al., A diffusion model explanation of the worst performance rule for reaction time and IQ. Intelligence. 2008. vol. 36: 10-17.
Arendash et al., Electromagnetic Field Treatment Protects Against and Reverses Cognitive Impairment in Alzheimer's Disease Mice. Journal of Alzheimer's Disease. 2010. vol. 19: 191-210.
Dragicevic et al., Long-term electromagnetic field treatment enhances brain mitochondrial function of both Alzheimer's transgenic mic and normal mice: a mechanism for electromagnetic field-induced cognitive benefit? Neuroscience. 2011. vol. 185: 135-149.
Arendash. Transcranial Electromagnetic Treatment Against Alzheimer's Disease: Why it has the Potential to Trump Alzheimer's Disease Drug Development. Journal of Alzheimer's Disease. 2012. vol. 32: 243-266.
Mori and Arendash. Long0Term Electromagnetic field treatment increases brain neuronal activity: Linkage to cognitive Benefit and Therapeutic Implications for Alzheimer's Disease. J Alzheimers Dis. 2011. vol. 1 (Issue 2): 1-4.
Sliwinska et al., Transcranial Magnetic Stimulation for Investigating Causal Brain-behavorial Relationships and their Time Course. Journal of Visualized Experiments. 2014. vol. 89: e51735.
Arendash et al., Electromagnetic Treatment to Old Alzheimer's Mice Reverses Beta-Amyloid Deposition, Modifies Cerebral Blood Flow, and Provides Selected Cognitive Benefit. PLOS One. 2012. vol. 7 (Issue 4): E35751.
Koren III et al., Chaperone signalling complexes in Alzheimer's disease. J Cell Mol Med. 2009. vol. 13 (No. 4): 619-630.
Jiang et al., Electromagnetic Pulse Exposure Induces Overexpression of Beta Amyloid Protein in Rats. Archives of Medical Research. 2013. vol. 44 (Issue 3): 178-184.
Joubert et al., Non Apoptosis is induced in Rat Cortical Neurons Exposed to GSM Phone Fields. Bioelectromagnetics. 2007. vol. 28: 115-121.

(56) References Cited

OTHER PUBLICATIONS

Preece et al., Effect of a 915-MHz simulated mobile phone signal on cognitive function in man. Int. J. Radiat. Biol. 1999. vol. 75 (No. 4): 447-456.
Arendash et al., Electromagnetic Field Treatment Protects Against and Reverses Cognitive Impairment in Alzheimer's Disease Mice, Journal of Alzheimer's Disease,19:191-210, 2010.
Gursky et al., Temperature-dependent beta-sheet formation in beta-amyloid peptide in water, Abstract, Biochim Biophys Acta 1476:93-102, 2000.
Arendash et al., Electromagnetic Treatment to Old Alzheimer's Mice Reverses Beta-Amyloid Deposition, Modifies Cerebral Blood Flow, and Provides Selected Cognitive Benefit, PLoS One 7(4): e35751, 2012.

\* cited by examiner

PREVENTION AND TREATMENT OF BRAIN DISEASES AND DISORDERS RELATED TO ABNORMAL PROTEIN AGGREGATION THROUGH ELECTROMAGNETIC FIELD TREATMENT

CROSS REFERENCE TO RELATED APPLICATIONS

This application is a continuation-in-part of and claims priority to U.S. Nonprovisional patent application Ser. No. 13/230,415, entitled "Prevention and Treatment of Alzheimer's Disease through Electromagnetic Field Exposure", filed Sep. 12, 2011, which is a continuation of and claims priority to PCT Patent Application Serial No. PCT/US2010/026952, entitled "Prevention, Treatment, and Diagnosis of Alzheimer's Disease Through Electromagnetic Field Exposure", filed Mar. 11, 2010, which claims priority to U.S. Provisional Patent Application Ser. No. 61/159,251, entitled "Electromagnetic Field Treatment Protects Against and Reverses Cognitive Impairment in Alzheimer's Mice", filed Mar. 11, 2009, all of which are incorporated herein by reference in their entireties.

GOVERNMENT SUPPORT

This invention was made with government support under Grant No. AG025711 awarded by the National Institutes of Health. The government therefore has rights in the invention.

BACKGROUND OF THE INVENTION

1. Field of the Invention

The invention relates to devices, methods, and systems that utilize electromagnetic waves within the ultra-high frequency range to provide therapeutic effects for the brain in preventing, ameliorating, or reversing neurologic diseases or disorders which are characterized by abnormal protein aggregation, most notably abnormal brain aggregation/deposition of β-amyloid (Aβ). The invention also relates to devices, methods, and systems for providing cognitive benefits to normal (unimpaired) individuals, as well as to those with age-associated cognitive impairment or sub-normal cognitive function.

2. Brief Description of the Prior Art

A variety of neurologic disorders involve abnormal amyloid protein aggregation or other abnormal protein aggregations in the brain. Primary among amyloid-aggregating disorders is Alzheimer's disease (AD), in which the protein β-amyloid (Aβ) is abnormally produced by neurons and deposited both within neurons in small oligomeric forms, as well as outside of neurons in fibrillary/forms. Many AD researchers believe that brain production and ensuing aggregation of β-amyloid (Aβ) is the root cause of the disease. Thus, any therapeutic that can disaggregate or prevent Aβ aggregation (oligomeric or fibrillary) could be of immense value to protect against or treat AD.

Another amyloid-related neurological disorder is Trisomy 21 (Down's syndrome). Invariably, Down's patients develop Aβ aggregations/plaques (very similar to those of AD), as they age. Moreover, Down's patients become even more cognitively impaired as these brain Aβ aggregations/plaques develop. It is therefore likely that therapeutics aimed at preventing or disaggregating brain Aβ aggregation/deposits could lessen or eliminate the further cognitive impairment experienced b Down's patients in their older age (i.e., generally their 30's).

A third amyloid-related neurological disorder is traumatic brain injury (TBI). The primary/initial injury induced by TBI is largely unavoidable, but triggers secondary brain injury over the hours/days following injury that may be readily treatable. In both humans and animals, a key component to this secondary injury is rapid brain accumulation of the protein β-amyloid (Aβ) in as little as one day after injury. Not surprisingly then, many TBI fatalities have brain Aβ aggregations (deposits) at autopsy. Since Aβ aggregation following TBI appears to be a key mediator of brain tissue loss and resulting cognitive dysfunction, therapeutics aimed at post-TBI suppression of Aβ aggregation could greatly limit secondary TBI injury and provide substantial functional recovery.

Other brain diseases/disorders in which Aβ aggregation/deposition occurs and is thought to be involved in the disease's pathophysiology include Mixed AD/Vascular Dementia, Cerebral Amyloid Angiopathy, Hemorrhagic Stroke, Multi-Infarct Dementia, Cerebral Traumatic Encephalopathy. There are currently no effective therapeutics to treat these conditions, so therapeutics that can disaggregate or prevent Aβ aggregation could have real prophylactic or treatment value.

There are a variety of other neurologic diseases/disorders that are characterized by abnormal aggregation/deposition of non-Aβ proteins, which are thought to aggregation in the same fashion as Aβ—namely, via establishment of hydrogen bonds between monomeric units to form β-pleated sheets. These diseases and their associated abnormally-aggregating protein include Parkinson's Disease (α-synuclein), Lewy Body Dementia (α-synuclein), Fronto-Temporal Lobe Dementia (phosphorylated tau), Huntington's Disease (huntingtin), Amyotrophic Lateral Sclerosis (SOD1) and various Prion Diseases such as Transmissive Sponiform Encephalopathy, Kuru, and Creutzfeldt-Jakob Disease priori protein). Even AD is characterized not only by brain aggregation of Aβ, but also by aggregation of phosphorylated-tau.

Conventional pharmacotherapy has thus far failed to slow or reverse AD adequately, and has minimally impacted the other aforementioned brain disorders characterized by abnormal amyloid aggregation or the aggregation of other abnormal proteins in the brain. There thus exists a need for non-pharmacologic devices, methods, and systems capable of providing effective therapeutic interventions against these disorders—all of which have the common feature of abnormal protein deposition in the brain.

In this regard, there are a variety of "neuromodulatory" approaches against AD that are currently being clinical investigated, including Transcranial Magnetic Treatment (tMT), Transcranial Direct Current Stimulation (tDCS), and Deep Brain Stimulation (DBS). All of these approaches simply stimulate existing neuronal circuitry and have not been demonstrated to affect the AD process (as it is currently understood). As the newest neuromodulatory approach against neurodegenerative diseases, Transcranial Electromagnetic Treatment (TEMT) offers distinct advantages, including deep/global brain treatment and disruption of the AD process. The inventors' preclinical work, beginning with their initial 2010 publication and extended greatly by four succeeding publications, forms the scientific basis for use of TEMT technology, as the invention described below, for the prevention and treatment of numerous neurologic diseases characterized by amyloid and non-amyloid protein aggregation in the brain.

After reviewing an extensive literature, the World Health Organization and other health councils/organizations have concluded that there are no adverse health risks to adults or children associated with electromagnetic fields (EMFs) within the Industry, Science, Medicine (ISM) band between 902-928 MHz, and more broadly between the 850-1900 MHz frequencies utilized by most present-day cell phones. However, there is little data concerning the long-term effects of these EMF frequencies on brain physiology and function. Epidemiologic studies have suggested that occupational (low frequencies around 60 Hz) EMF exposure may increase risk of Alzheimer's Disease (AD), while other studies have found that acute exposure to cell phone (high frequencies of 850-1900 MHz) EMF has essentially no effect, or a limited effect, on cognitive function in normal individuals. To date, no controlled long-term studies of EMF effects on cognitive function have been done in humans or humans with Alzheimer's disease. However, the inventors have performed multiple studies involving transgenic mouse models for AD with EMF frequencies in the ISM band that have clearly shown that long-term EMF treatment to these AD mice results in cognitive protection or reversal of cognitive impairment. In these same animals, they have shown that EMF not only prevents or reverses brain Aβ aggregation, but it also enhances mitochondrial function and increases neuronal activity. These findings are detailed below in the Detailed Description of the Preferred Embodiment.

SUMMARY OF INVENTION

This invention is the first to use long-term EMF exposure within the UHF range to provide treatment for neurological disorders as well as preventative cognitive benefits. Both cognitive-protective and cognitive-treatment effects of EMF exposure are demonstrated herein for young adult Alzheimer's transgenic (Tg) mice and older Tg mice, respectively. Even normal mice were shown to receive cognitive benefits from EMF treatment. In Alzheimer's Tg mice, long-term EMF treatment reduced brain β-amyloid (Aβ) deposition through Aβ anti-aggregation actions that were confirmed in brain homogenate studies. Evidence for several inter-related mechanisms of EMF action are proposed in the brain, including disaggregation of both oligomeric and fibrillary Aβ, mitochondrial enhancement, and increased neuronal activity. Accordingly, the invention includes the use of EMF exposure as a non-invasive, non-pharmacologic therapeutic against AD and other abnormal protein-aggregating disorders, as well as an effective memory-enhancing approach in general.

According to a first embodiment the invention includes a method of treating a neurological disorder, such as Alzheimer's Disease, in a subject in need thereof by positioning an electromagnetic field emitting source proximal to the subject and exposing the subject to an electromagnetic field having a predetermined frequency for a predetermined absorption period. Preferably, each individual treatment (comprising exposure to the predetermined frequency for the predetermined absorption period) is continued at a predetermined schedule (preferably daily) for a predetermined treatment period of days, weeks, months, or years.

The predetermined frequency, according to a preferred embodiment, is within the ultra-high frequency (UHF) range of 300-3,000 MHz (continuous or pulsed, with or without modulation), with a specific absorption rate (SAR) of up to 8 W/kg. The predetermined absorption period of this preferred embodiment is about one hour per treatment session, twice daily. The treatment period is long-term, typically being greater than one week and likely being months or years for therapeutic efficacy. It is understood that this invention covers any variations in treatment periods, such as alternate days and/or any other intermittent/recurring treatment periods.

The invention also includes, in a second embodiment, a method of preventing or treating an amyloid-related neurological disorder by positioning an electromagnetic field emitting source proximal to the subject and exposing the subject to an electromagnetic field having a predetermined frequency for a predetermined absorption period. Preferably, each individual treatment (comprising exposure to the predetermined frequency for the predetermined absorption period) is continued at a predetermined schedule (preferably daily) for a predetermined treatment period.

The predetermined frequency, according to a preferred embodiment, is within the UHF range of 300-3,000 MHz (continuous or pulsed, with or without modulation), with a specific absorption rate (SAR) of up to 8 W/kg. The predetermined absorption period of this preferred embodiment is about one hour per treatment session, twice daily. The treatment period is long-term, typically being greater than one week and likely being months or years for therapeutic efficacy. It is understood that this invention covers any variations in treatment periods, such as alternate days and/or any other intermittent/recurring treatment periods.

The invention also includes, in a third embodiment, a method of preventing or treating a neurologic disorder involving abnormal aggregation of non-Aβ proteins by positioning an electromagnetic field emitting source proximal to the subject and exposing the subject to an electromagnetic field having a predetermined frequency for a predetermined absorption period. Preferably, each individual treatment (comprising exposure to the predetermined frequency for the predetermined absorption period) is continued at a predetermined schedule (preferably daily) for a predetermined treatment period.

The predetermined frequency, according to a preferred embodiment, is within the UHF range of 300-3,000 MHz (continuous or pulsed, with or without modulation), with a specific absorption rate (SAR) of up to 8 W/kg. The predetermined absorption period of this preferred embodiment is about one hour per treatment session, twice daily. The treatment period is long-term, typically being greater than one week and likely being months or years for therapeutic efficacy. It is understood that this invention covers any variations in treatment periods, such as alternate days and/or any other intermittent/recurring treatment periods.

The invention also includes, in a fourth embodiment, a method of enhancing cognitive function in normal, unimpaired individuals, as well as those with Age-Associated Memory Impairment (AAMI) or sub-normal cognitive function, by positioning an electromagnetic field emitting source proximal to the subject and exposing the subject to an electromagnetic field having a predetermined frequency for a predetermined absorption period. Preferably, each individual treatment (comprising exposure to the predetermined frequency for the predetermined absorption period) is continued at a predetermined schedule (preferably daily) for a predetermined treatment period.

The predetermined frequency, according to a preferred embodiment, is within the UHF range of 300-3,000 MHz (continuous or pulsed, with or without modulation), with a specific absorption rate (SAR) of up to 8 W/kg. The predetermined absorption period of this preferred embodiment is about one hour per treatment session, twice daily. The treatment period is long-term, typically being greater than one week and likely being months or years for therapeutic efficacy. It is understood that this invention covers any variations in treatment periods, such as alternate days and/or any other intermittent/recurring treatment periods.

BRIEF DESCRIPTION OF THE DRAWINGS

For a fuller understanding of the invention, reference should be made to the following detailed description, taken in connection with the accompanying drawings, in which:

FIGS. 1A-1D show that EMF exposure, begun in young adulthood, protects Alzheimer's Tg mice from cognitive impairment and improves basic memory of normal mice.

FIGS. 5A-5D show that at 8 months into EMF exposure, cognitively-impaired Alzheimer's Tg mice exhibited cognitive benefits and reduced brain Aβ deposition.

DETAILED DESCRIPTION OF THE PREFERRED EMBODIMENT

Figure 1A:
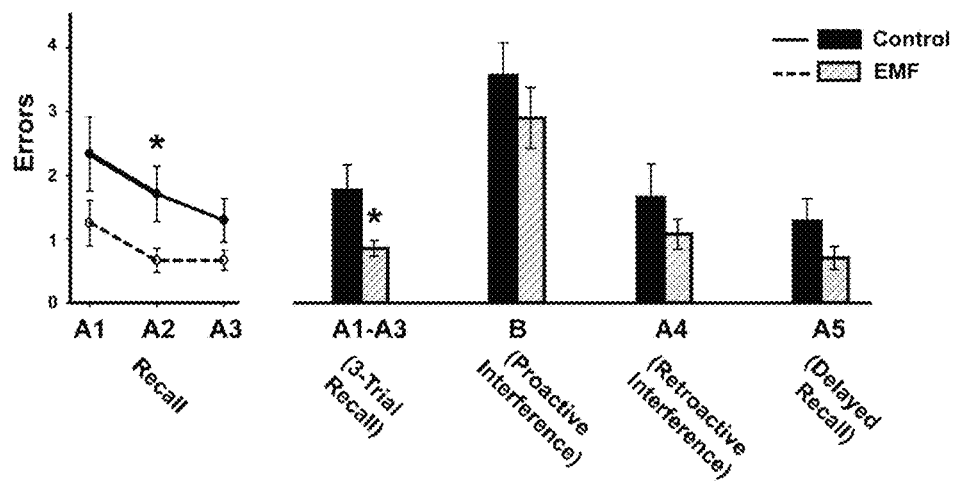
FIG. 1A depicts cognitive interference testing at 4-5 months into EMF exposure revealed overall cognitive benefits at the initial test point and cognitive protection of Tg mice at the later test point during Block 1.

In certain embodiments, the current invention provides an extension of U.S. patent application Ser. No. 13/230,415 by expanding the EMF treatment frequency to include the entire ultra-high frequency (UHF) range, increasing the power (Specific Absorption Rate; SAR) levels for EMF treatment, extending the EMF modalities/signals being utilized to pulsed with or without modulation, and extending the neurologic conditions for which the treatment has applicability. Alternatively, the EMF modalities/signals can be continuous with or without modulation.

The invention includes, in a general embodiment, a method of treating and/or preventing any β-amyloid-related neurological disorder (such as AD, TBI, and/or Down's Syndrome) by exposing a subject to ultra-high frequency EMF for a predetermined treatment period. An amyloid-related neurological disorder is any disorder which is characterized by aberrant β-amyloid activity. In addition to AD, TBI, and Down's Syndrome, examples of amyloid-related neurological disorders include Mixed AD/Vascular Dementia, Cerebral Amyloid Angiopathy, Hemorrhagic Stroke, Multi-Infarct Dementia, and Cerebral Traumatic Encephalopathy. The term "preventing" includes both total prevention of the onset of the amyloid-related neurological disorder as well as reducing the degree of the effects of such disorder. The term "treatment" embodies alleviation of both brain pathology and behavioral symptoms in individuals who already have a β-amyloid-based neurological disorder.

In a preferred embodiment the treatment period is long term, generally spanning months or years. The predetermined frequency, according to a preferred embodiment, encompasses the UHF range of about 300-3,000 MHz, with a specific absorption rate (SAR) of up to 8 W/kg. The predetermined absorption period of this preferred embodiment is about one hour, twice daily. The treatment period is long-term, generally greater than one week and typically for months or years. The term "about" is not meant to limit the invention to a strict numerical interpretation and includes ranges of the relevant parameter which does not materially affect the basic and novel characteristics of the invention.

To elucidate the effects of long-term (7-9 months) EMF exposure on AD-like cognitive impairment and neuropathology, the inventors exposed Alzheimer's transgenic (Tg) mice and littermate non-transgenic (NT) mice to EMFs at 918 MHz (pulsed and modulated) and 0.25-1.05 W/kg SAR. Here the inventors show that such twice daily (for ~1 hour each) EMF exposure: 1) protects young adult Tg mice from later cognitive impairment, 2) reverses cognitive impairment and AD-like brain pathology in older Tg mice, and 3) increases cognitive performance of normal NT mice. The novel behavioral task utilized to reveal these cognitive benefits was designed and implemented to closely mimic (measure-for-measure) a human "cognitive interference" task, which very effectively discriminates AD, mild cognitive impairment (MCI), and non-demented individuals.

Figure 1B:
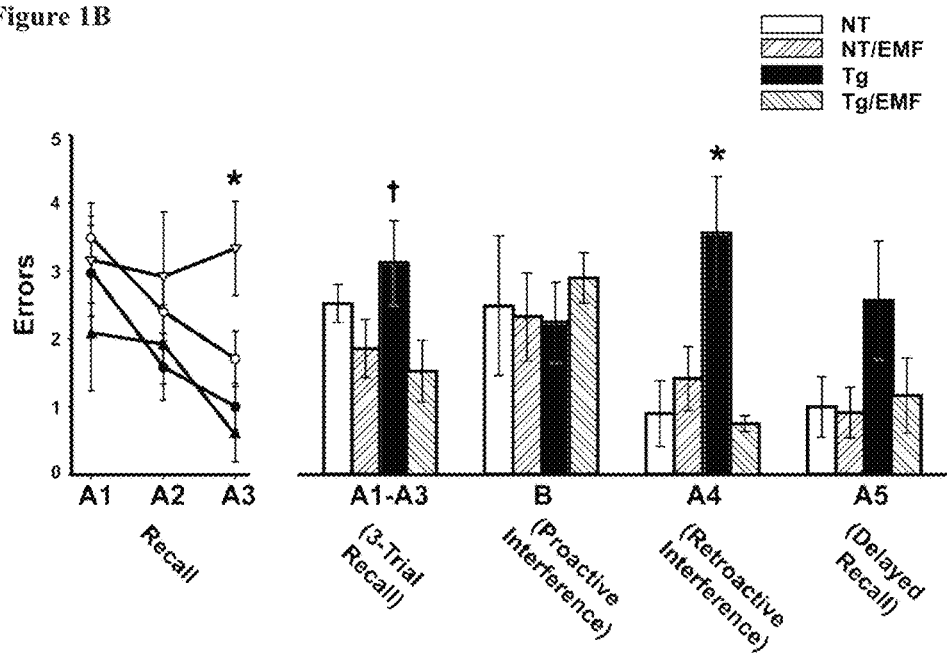
FIG. 1B depicts cognitive interference testing at 6-7 months into EMF exposure revealed overall cognitive benefits at the initial test point and cognitive protection of Tg mice at the later test point during Block 1.
Figure 1C:
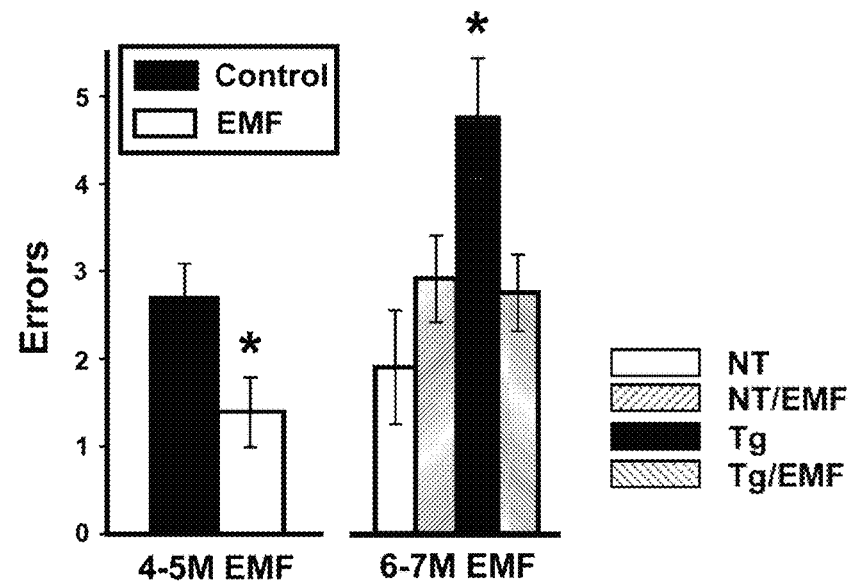
FIG. 1C depicts proactive interference testing during Block 2 revealing both overall benefit (at 4-5M) and cognitive protection of Tg mice (at 6-7M). *P<0.05 vs. other group(s) at same timepoint; †P<0.05 vs. Tg/EMF group.
Figure 1D:
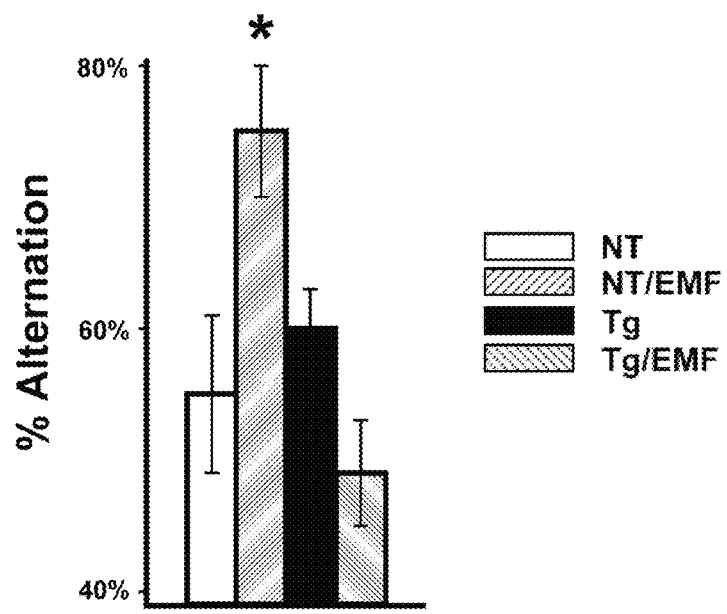
FIG. 1D depicts that normal mice at 6-7 months into EMF exposure showed superior Y-maze spontaneous alternation. *P<0.05 vs. all other groups. Overall.

In an initial "young adult" long-term study, 2-month old Tg and NT mice were started on daily EMF exposure for the next 7 months, with cognitive testing performed at 4-5 and 6-7 months into EMF exposure (see Examples 1, 2 and 5 below). During the first test period, there were no effects of transgenicity on cognitive interference performance. Therefore, NT and Tg groups were combined into EMF treatment and non-treatment groups, which elucidated significantly better performance of EMF-exposed mice during 3-trial recall testing compared to non-exposed mice (FIG. 1A). By the second test period (2 months later), Tg control mice were impaired in not only 3-trial recall, but also in retroactive interference compared to the excellent performance of both NT groups (FIG. 1B). By contrast, Tg mice that had been receiving chronic EMF exposure for 7 months showed significantly better performance than Tg controls—not only at the end of recall (A3), but also for "overall" 3-trial recall (A1-A3) and retroactive interference (A4). Although all 4 groups performed at the same mediocre level during early proactive interference testing (FIG. 1B), later proactive interference testing at both 4-5 month and 6-7 month time points revealed overall protection for EMF-exposed mice and strikingly better performance of Tg/EMF mice compared to Tg controls, respectively (FIG. 1C). In a final task of general mnemonic function prior to euthanasia, normal NT mice that had been given chronic EMF exposure for 7 months showed much higher Y-maze spontaneous alternation than control NT mice, which performed similar to Tg mice (FIG. 1D). Thus, EMF exposure begun in young adulthood completely protected Tg mice from otherwise certain cognitive impairment and even enhanced cognitive performance of normal NT mice. Although animals were euthanized prior to overt Aβ deposition, near significant increases in levels of soluble Aβ were evident in the hippocampus and frontal cortex of EMF-exposed Tg mice (see Table 1 and Example 7). These nearly significant increases in brain Aβ are consistent with the ability of EMF treatment to disaggregate oligomeric clusters of Aβ, resulting in greater numbers of smaller Aβ monomers and dimers.

Figure 2:
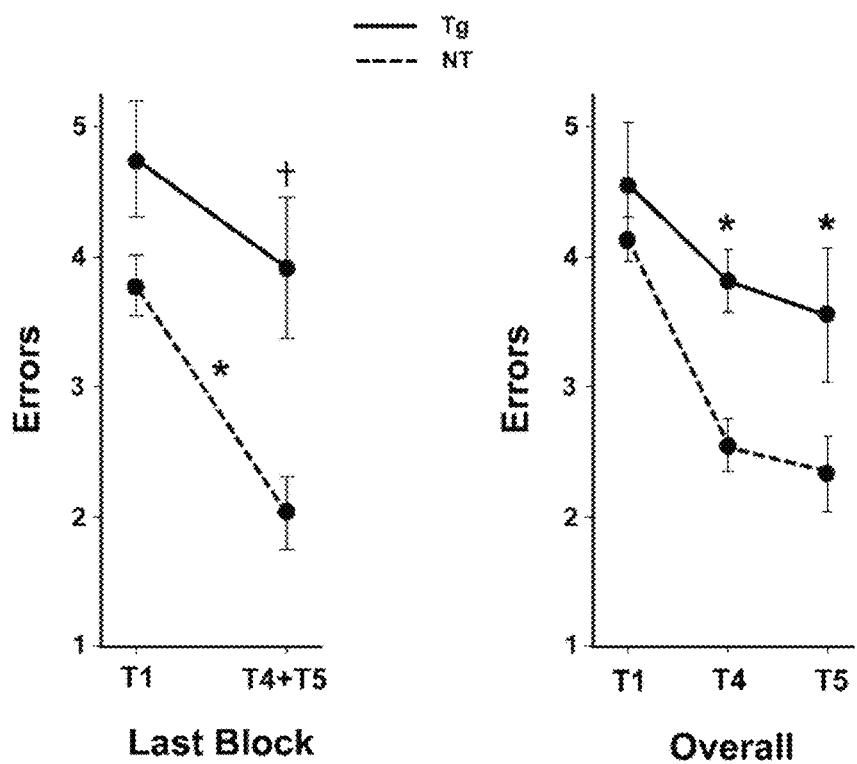
FIG. 2 depicts results of an Aged Adult Long-term Study, where Tg mice are impaired in cognitive function prior to EMF exposure. RAWM working memory performance during the last of three 2-day test blocks (left) and over all 3 blocks (right), is shown for NT and Tg mice tested at 4 months of age. Left graph: *P<0.0005 for T1 vs. T5; †P<0.005 vs. NT group. Right graph: *P<0.05 or higher level of significance vs. NT group.
Figure 3:
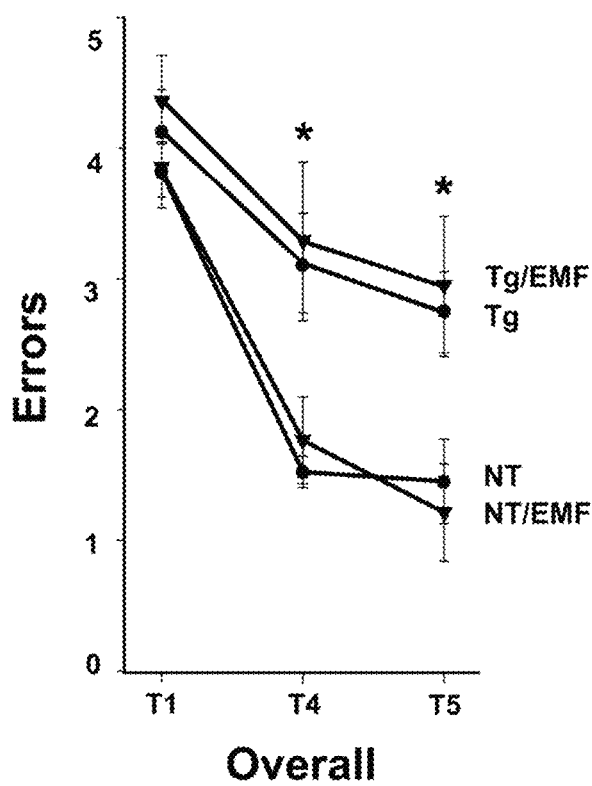
FIG. 3 depicts results of an Aged Adult Long-term Study, where the first two months of EMF exposure does not result in cognitive benefit to impaired Tg mice. EMF exposure had no effect on RAWM working memory performance of either NT or Tg mice over all 14 days of testing, with both groups of Tg mice being impaired on working memory trials T4 and T5 vs. both groups of NT mice. *P<0.02 or higher level of significance for both Tg groups vs. both NT groups.
Figure 4:
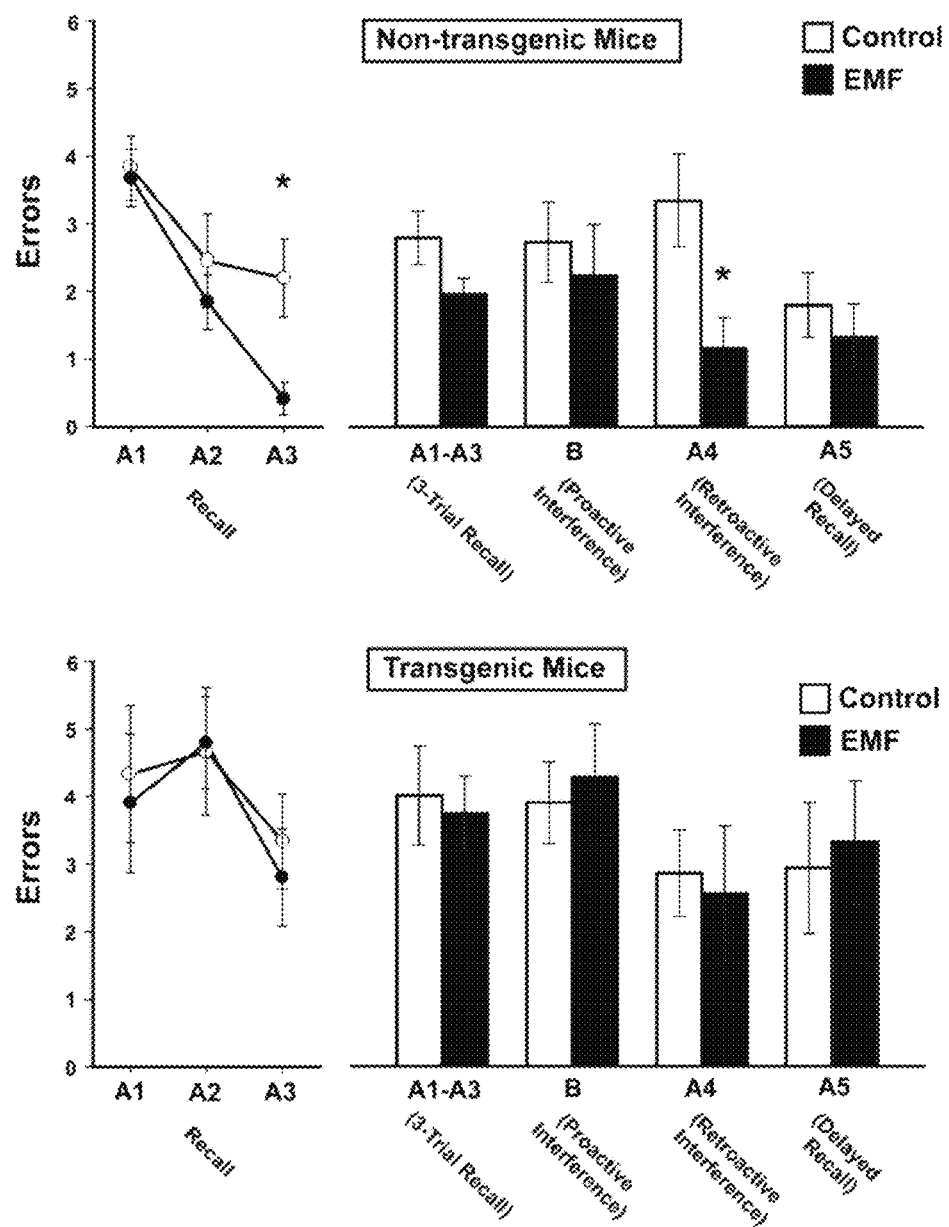
FIG. 4 depicts results of an Aged Adult Long-term Study, where at five months into long-term EMF exposure, no deleterious or beneficial effects were evident in cognitive interference testing of Tg mice, although normal (NT) mice showed EMF-induced cognitive benefits in some measures. Data for the final two-day block of testing are presented. *P<0.05 vs. NT control

To determine if EMF treatment could reverse cognitive impairment and brain β-amyloid (Aβ) pathology in older Alzheimer's Tg mice, the inventors exposed 5-month old mice to daily EMF treatment for the following 8 months. In an "aged adult" long-term study, cognitive testing was performed before the start of EMF treatment, as well as at 2 months, 5 months, and 8 months into EMF treatment (Examples 1, 3 and 5). During pre-exposure cognitive testing at 4 months of age, naïve Tg mice were clearly impaired in the radial arm water maze (RAWM) task of working memory (FIG. 2). Re-testing of mice in this same RAWM task at 2 months into EMF treatment (FIG. 3), as well as in the cognitive interference task at 5 months into EMF treatment (FIG. 4), showed no beneficial effects of EMF on cognitive performance of Tg mice. In NT mice, however, cognitive interference performance was significantly improved at 5 months into exposure (FIG. 4).

Figure 5A:
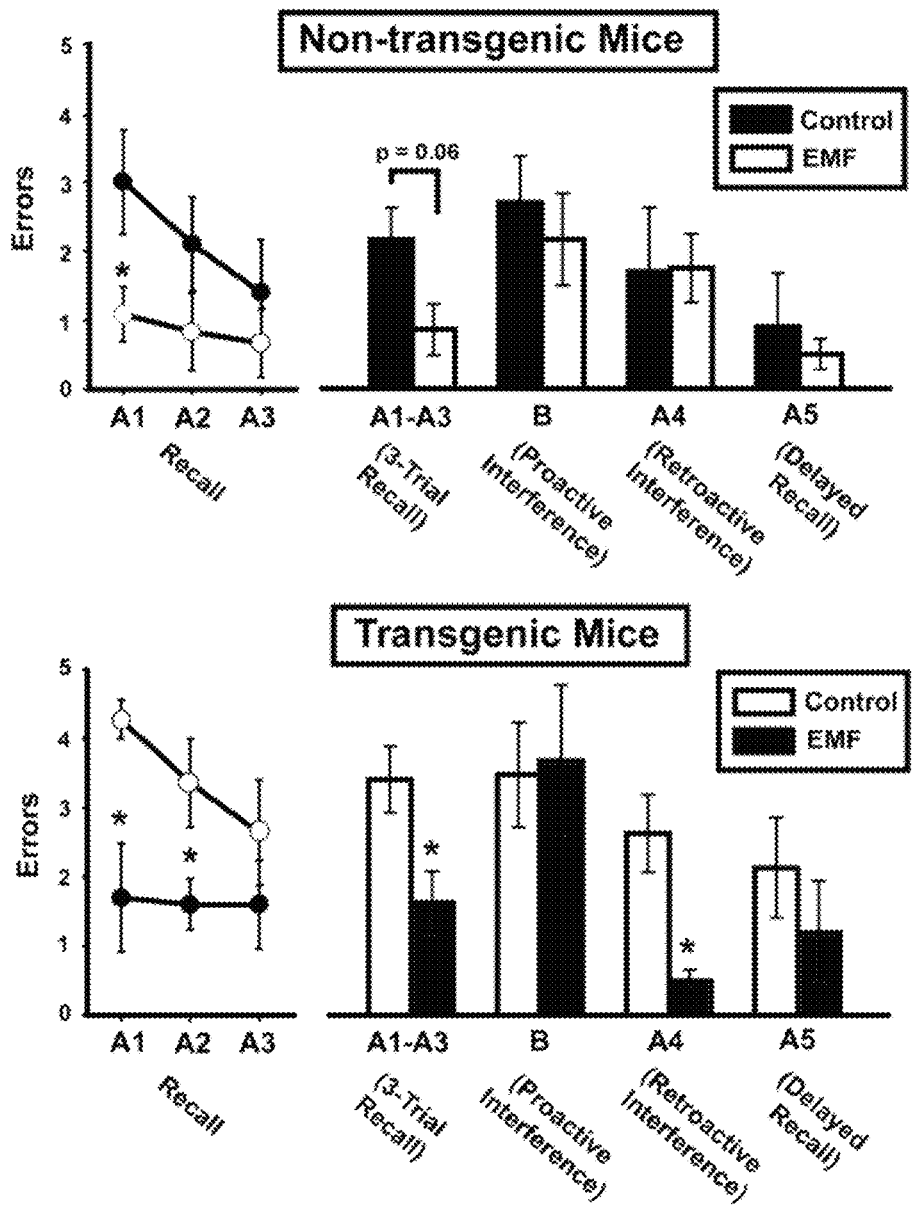
FIG. 5A shows that cognitive interference testing revealed Tg/EMF mice as vastly superior to Tg controls in 3-trial recall and retroactive interference performance. Even NT mice receiving EMF exposure showed better recall performance than NT controls, particular early in recall testing. The final 2-day block of testing is shown from four days of testing. Upper graph: *P<0.025 vs control; Lower graph: *P<0.05 or higher level of significance vs. control.
Figure 5B:
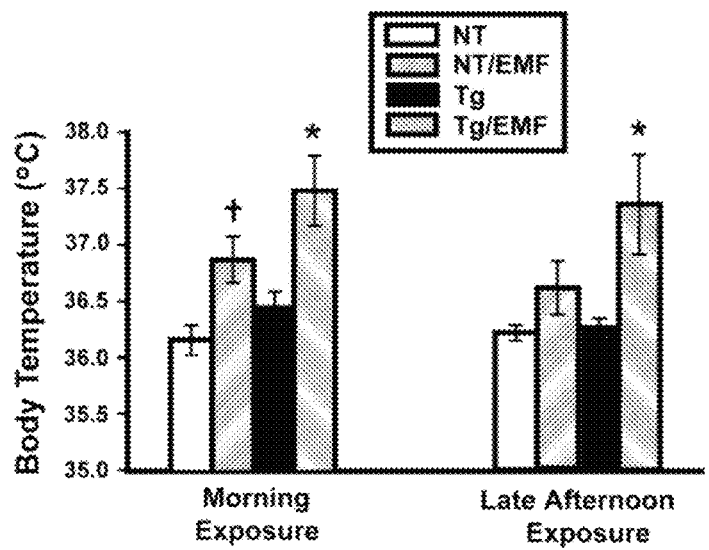
FIG. 5B shows that during both 1-hour EMF exposure periods in a given day at 8 months into exposure, Tg mice exhibited significantly higher body temperatures compared to mice in all other groups. NT/EMF exhibited marginally-higher body temperatures levels during the morning exposure. *P<0.05 or higher levels of significance vs. all other groups; †P<0.05 vs. NT group.

After 8 months of EMF treatment, all mice were re-evaluated in the cognitive interference task of working memory (FIG. 5). At this 13 month age, non-treated Tg control mice were noticeably impaired while the cognitive performance of Tg mice receiving EMF exposure was strikingly better (FIG. 5A, lower). On 3-trial recall, Tg/EMF mice performed significantly better than Tg controls overall and even on the initial recall trials. In addition, Tg/EMF mice showed vastly superior retroactive interference performance compared to Tg controls. Even NT mice continued to show cognitive benefits from ongoing EMF exposure through 8 months (FIG. 5A, upper). In fact, profound beneficial effects of EMF exposure on 3-trail recall were evident irrespective of genotype (FIG. 6).

Figures 7A, 7B:
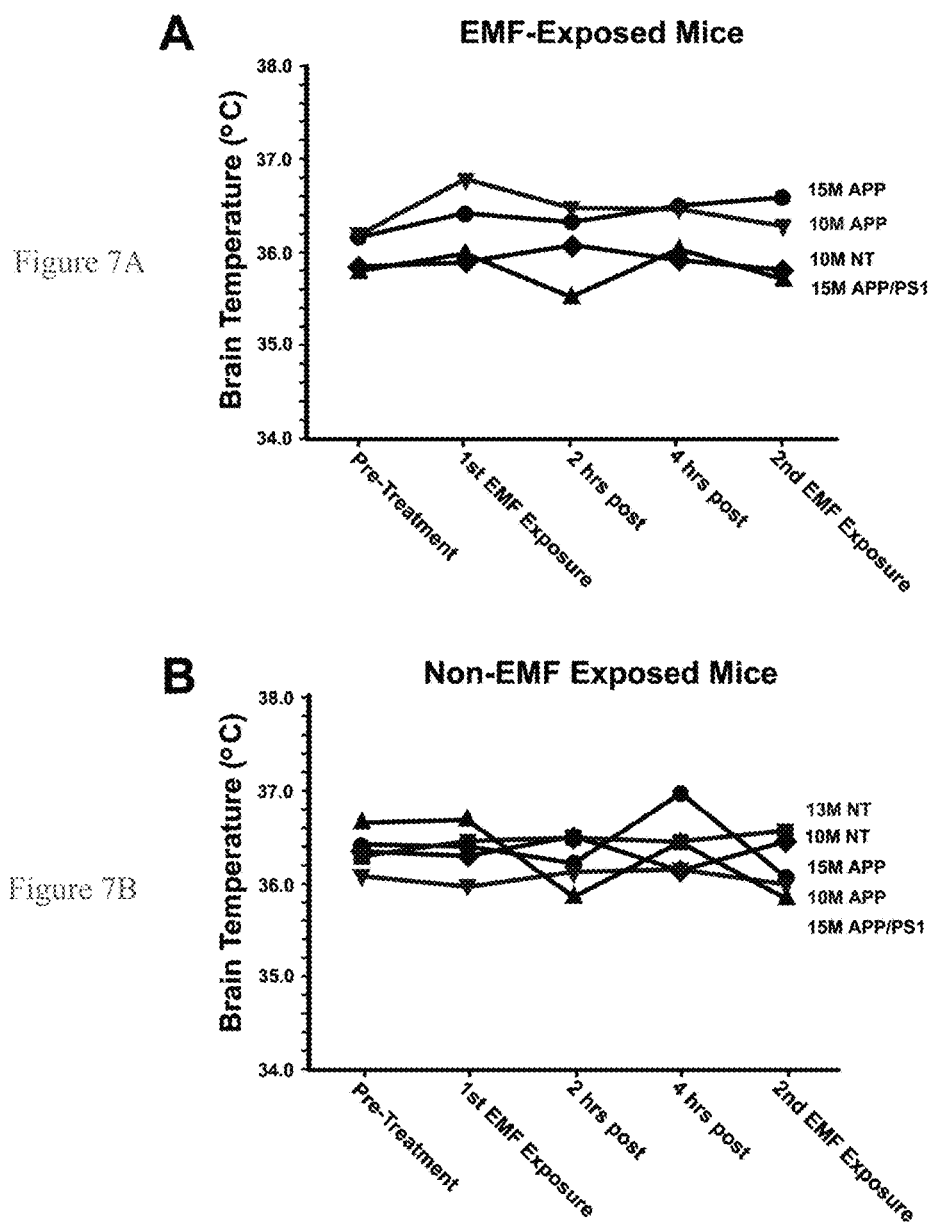
FIG. 7A depicts brain temperature (as measured by temporal muscle probe) before, during, and between EMF exposure in nave mice of various genotypes and ages. Measurements were all recorded during a single day, with identical results attained on several other single day EMF exposures (not shown), all done within a two-week period. Each measurement represents the mean of 4-5 mice per group.
FIG. 7B depicts brain temperature (as measured by temporal muscle probe) before, during, and between EMF non-exposure in naïve mice of various genotypes and ages.

Because it is well-known that EMF exposure can increase body/tissue temperature, the inventors monitored body temperature via rectal probe during a single day of EMF exposure just prior to euthanasia of mice in the adult long-term study (i.e., at 8½ months into EMF exposure). Compared to animals in all other groups, Tg mice being given EMF exposure had significantly higher body temperature (over 1° C. higher) for both early morning and late afternoon EMF exposures (FIG. 5B). During the "off" period between the two EMF exposures, no group differences in body temperature were observed. Thus, body temperatures of Tg mice were elevated only during "on" periods of EMF exposure. To determine if this hyperthermic response to long-term EMF exposure is also induced by acute EMF exposure and if body temperature was accurately reflecting brain temperature in the inventor's mice, an additional study was performed over a single day in naïve aged mice (Example 4). No effects of acute EMF exposure on brain or body temperature were evident for Tg or NT mice of several ages (FIGS. 7A-7B), indicating that long-term EMF exposure was required for the increased body temperature seen in Tg mice during "on" periods.

Figure 5C:
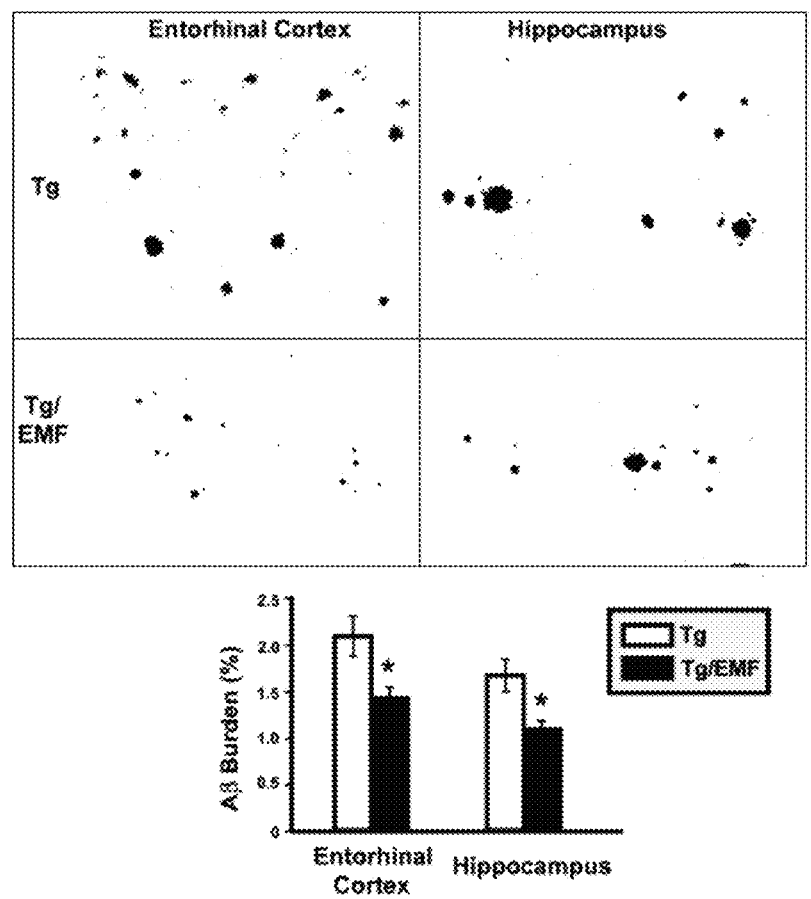
FIG. 5C shows that long-term EMF exposure significantly reduced total Aβ deposition in entorhinal cortex and hippocampus of Tg mice. Photomicrographic examples of typical Aβ immunostained-plaques from Tg and Tg/EMF are provided. *P<0.02 vs. Tg control group. Scale bar=50 μM.
Figure 5D:
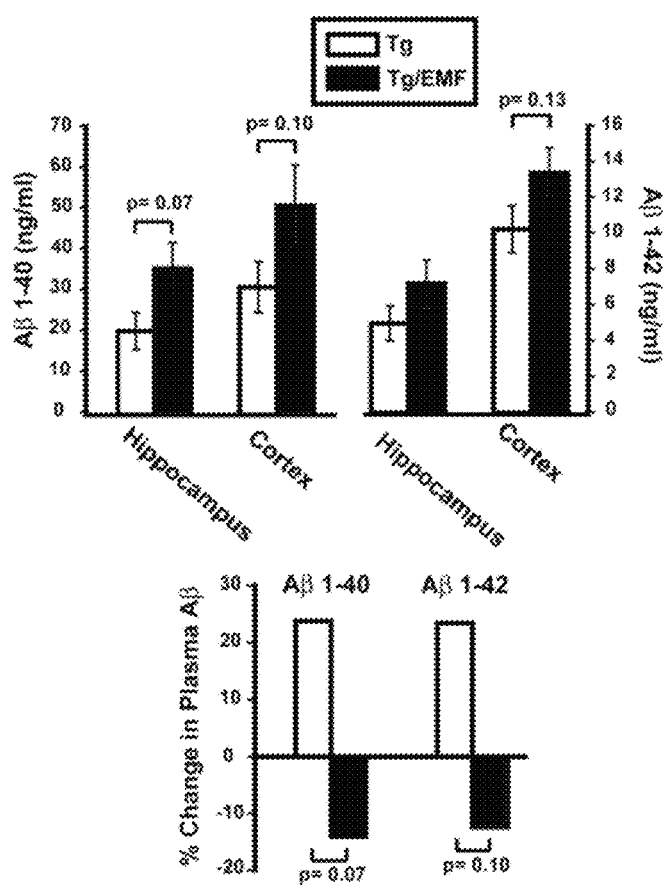
FIG. 5D shows that long-term EMF exposure nearly increased soluble Aβ levels in brain, while decreasing Aβ levels in plasma. Percent change in plasma Aβ measures involved comparison between pre-treatment blood Aβ levels at 5 months of age vs. Aβ levels attained at euthanasia (e.g., following 8+ months of EMF exposure). Overall.
Figure 6:
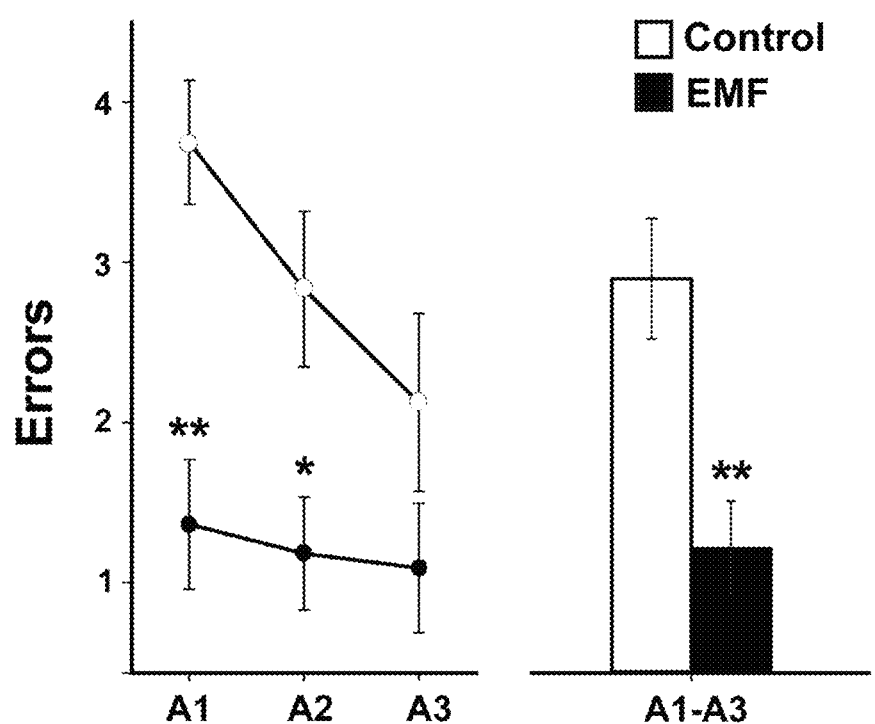
FIG. 6 depicts results of an Aged Adult Long-term Study, where robust cognitive benefits of 8-months EMF exposure were evident in cognitive interference testing, irrespective of genotype (combined NT and Tg groups). Depicted are individual recall trials and the average of all 3 recall trials for the final 2-day block of testing. *P<0.02 vs control group; *P<0.005 vs control group.

After euthanasia at 13½ months of age, Aβ immunostaining (Example 7) from Tg mice revealed substantially lower Aβ burdens in both hippocampus (↓35%) and entorhinal cortex (↓32%) of EMF-exposed Tg mice compared to Tg controls (FIG. 5C). These same EMF-exposed Tg mice exhibited nearly significant increases in hippocampal and cortical levels of soluble Aβ (FIG. 5D; Example 7). These nearly-significant increased levels of soluble Aβ in brain are consistent with the ability of EMF treatment to disaggregate oligomeric clusters of Aβ, resulting in greater numbers of smaller Aβ monomers and dimers. Long-term EMF exposure in Tg mice concurrently induced nearly-significant decreases in plasma Aβ1-40 and Aβ1-42 levels compared to Tg controls (FIG. 5D).

Figure 8A:
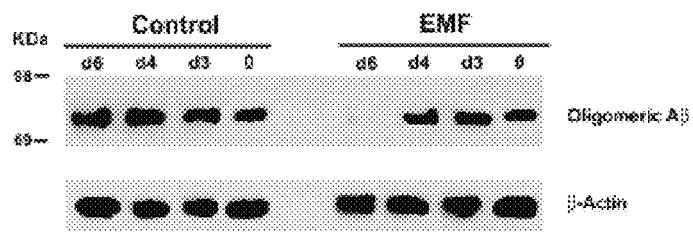
FIG. 8A depicts in vitro EMF exposure of hippocampal homogenates from Tg mice results in progressively decreased Aβ aggregation (oligomerization) between 3 and 6 days into exposure. Western blots display the 80 kDa Aβ oligomer on top and the β-Actin protein control on bottom. Left panel shows non-treated Tg controls of Aβ aggregation, while tight panel shows the same homogenates exposed to EMF treatment through 6 days.

There are several mechanisms, separately or in combination, that are most likely involved in the beneficial impact of EMF exposure on AD-like cognitive impairment/Aβ neuropathology in Tg mice and on cognitive performance in normal mice. A first mechanism would be an ability of EMF exposure to suppress Aβ aggregation and/or to disaggregate pre-existing Aβ associated Aβ oligomers and Aβ neuritic plaques in Tg mice. Consistent with this mechanism is the presently-reported EMF-induced decrease in brain Aβ deposition in aged Tg mice, along with their nearly significant increases in soluble brain Aβ levels. To explore the anti-Aβ aggregating potential of EMFs, the inventors sonicated hippocampal homogenates from aged 14 month old Tg mice to disaggregate their Aβ. They then subjected these homogenates to the same EMF strength/parameters as in the inventor's in vivo studies (Example 8). By four days into EMF treatment, substantially less aggregated (oligomeric) Aβ was evident by Western blots compared to non-exposed hippocampal homogenates (FIG. 8A). This is the first demonstration that UHF-range EMF treatment (more specifically in the ISM band of 902-928 MHz) can decrease brain Aβ aggregation.

The delayed ability of EMF treatment to benefit cognitive performance in adult Tg mice (e.g., manifesting itself at 8 months into exposure), likely reflects the time required for the currently-used EMF parameters to significantly impact the dynamic equilibrium between deposited/insoluble and soluble Aβ in the brain (FIG. 8B), such that Aβ could be cleared from the brain.

Figure 8B:
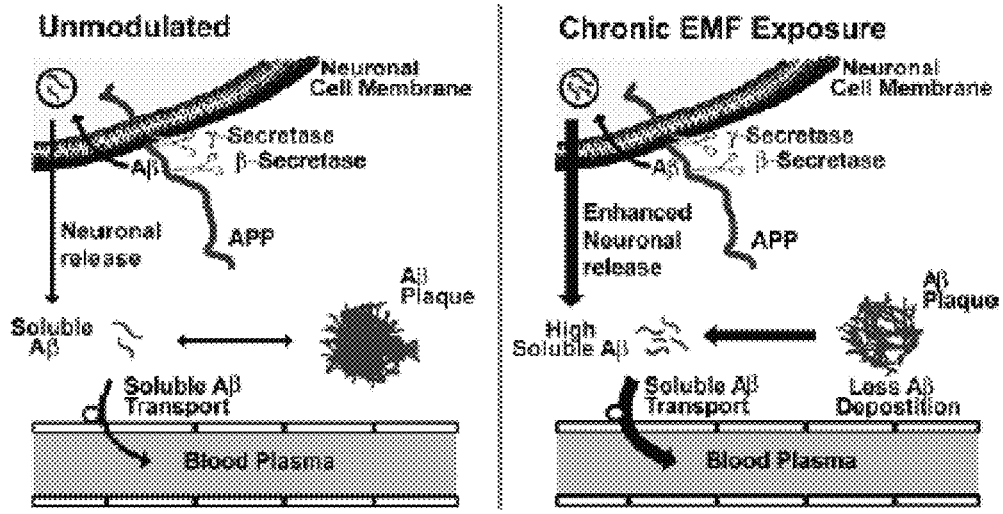
FIG. 8B shows diagrams depicting the proposed inhibitory actions of long-term EMF exposure on Aβ aggregation and stimulation of neuronal Aβ release in aged Tg mice, resulting in higher interstitial fluid Aβ levels and increased brain clearance of Aβ.

A second mechanism of action (for both AD Tg and normal mice) involves the ability of EMF exposure to increase neuronal/EEG activity. This ability is underscored by studies showing that EMF exposure within the ISM Band (~902-928 MHz) increases cortical PET signaling, as well as the inventor's own studies (See Example 11). With regard to Aβ and AD Tg mice, amyloid precursor protein (APP) in pre-synaptic neuronal cell membranes is internalized via endocytosis, after which Aβ is cleaved and available for release during neuronal activity (FIG. 8B). Increased neuronal activity has been shown to result in greater synaptic release of this intracellular Aβ into brain ISF, which would make it available for transcytotic transport out of the brain.

Figure 9:
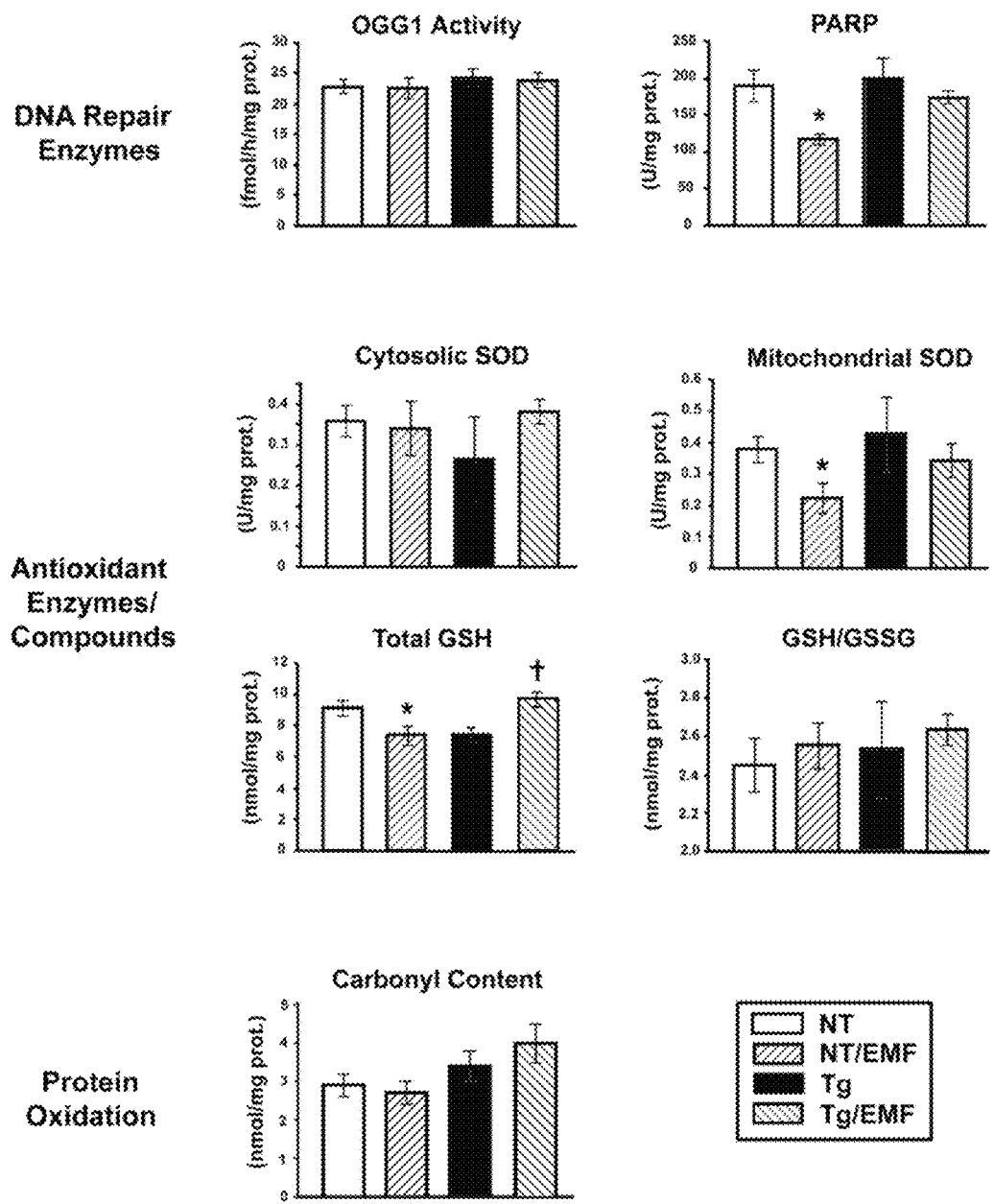
FIG. 9 depicts results of a Young Adult Long-term Study, where markers of oxidative damage and antioxidant enzymes/compounds in hippocampus were largely unaffected by long-term EMF exposure in Tg mice. NT/EMF mice exhibited a decreased level of the DNA repair enzyme PARP and suppressions in some antioxidant enzymes/compounds, but no changes in brain oxidative damage. This constellation of EMF effects in NT mice can actually be interpreted as a decrease in oxidative stress. *P<0.05 vs. NT controls. Abbreviations: GSH, reduced glutathione; GSH/GSSG, ratio of reduced to oxidized glutathione; OGG1, 8-oxoguanine glycosylase; PARP, poly ADP-ribose polymerase; SOD, superoxide dismutase.

The inventor's analysis of oxidative markers from brains of mice in the young adult long-term study (exposed to EMFs for 6-7 months) revealed minimal or no EMF-induced effects on DNA repair enzymes, antioxidant enzymes, or extent of protein oxidative damage (FIG. 9). These results are consistent with a prior study involving cell phone EMF exposure to rabbits for 7 days, wherein no effects on brain oxidative markers were seen (see M. Kemal-Irmak et al., *Cell Biochem. and Function* 20, 279 (2002)). The inventors infer that minimal/no brain oxidative damage results from chronic EMF exposure within the ISM ~902-928 MHz range or that compensatory mechanisms come into play during long-term EMF exposure that largely negate any acute EMF-induced increases in oxidative stress/damage.

The presently reported beneficial effects of EMF exposure in both NT and Tg mice were largely observed after months of EMF exposure. In contrast to the cognitive improvement shown by EMF-exposed "normal" NT mice in the inventor's study, prior studies involving acute (7-14 days) EMF exposure to normal rodents failed to show any effects on cognitive performance (see Z. Sienkiewicz et al., *Bioelectromagnetics* 21, 151 (2000) and D. Dubreuil, T. Jay, J-M Edeline, *Behav. Brain Res.* 145, 51 (2003)). A limited daily (15-45 minute/day) and total EMF exposure length, different SAR levels, or use of different cognitive assessments could have been confounding factors in these earlier studies. In normal humans, short-term EMF exposure studies have also failed to demonstrate enhanced cognitive performance (Kwon and Hamalainen, *Bioelectromagnetics* 32, 253 (2011)). In view of these and the inventor's present findings, the inventors propose that only long-term EMF exposure may provide cognitive benefits to humans. Second, the inventors propose that such EMF exposure has the capacity to enhance cognitive function in normal, non-demented individuals, including those with Age-Associated Memory Impairment (AAMI), and those in the lower range of normal.

To date, there is no evidence that ultra-high frequency EMFs affect the risk of AD. Indeed, this specification provides striking evidence for both protective and disease-reversing effects of such long-term EMF exposure, and in an established transgenic model for both AD and Aβ production/deposition.

Example 1—Animals

A total of 96 mice, derived from the Florida Alzheimer's Disease Research Center's colony, were included in these studies. Each mouse had a mixed background of 56.25% C57, 12.5% B6, 18.75% SJL, and 12.5% Swiss-Webster. All mice were derived from a cross between heterozygous mice carrying the mutant APPK670N, M671L gene (APPsw) with heterozygous PS1 (Tg line 6.2) mice, which derived offspring consisting of APP/PS1, APPsw, PS1, and non-transgenic (NT) genotypes. After weaning and genotyping, APPsw and NT mice were selected for behavioral studies, while temperature-monitoring studies also included APP/PS1 mice. All mice were maintained on a 12-hour dark and 12-hour light cycle with ad libitum access to rodent chow and water. All animal procedures were performed in AAALAC-certified facilities under protocols approved by the USF Institutional Animal Care and Use Committees.

Example 2—Young Adult Long-Term Study

A total of 24 APPsw (Tg) mice and non-transgenic (NT) littermates, aged 2-2½ months, were divided into the following four groups: Tg controls, Tg+EMF, NT controls, NT+EMF (n=6 per group) All APPsw mice were screened for plasma Aβ levels and both Tg groups were balanced in terms of plasma Aβ levels. Tg and NT mice exposed to EMFs were housed in cages within a large Faraday cage, which also housed the antenna of an EMF generator providing two 1-hour periods of electromagnetic waves per day (early morning and late afternoon) within the ISM band frequency range of 902-928 MHz (typically 918 MHz), pulsed and modulated, 0.25-1.05 W/kg. At 6½ and at 9 months of age (4-5 and 6-7 months into EMF exposure), all mice were evaluated in a cognitive interference task (see Behavioral Test Protocols below) that closely parallels, and was designed from, a cognitive interference task utilized in humans to differentiate aged non-demented, MCI, and AD patients from one another (1). Behavioral testing always occurred during "OFF" periods of EMF exposure cyclicity (e.g., during the lights on period between any two exposure periods). After cognitive interference testing at 9 months of age, all animals were tested for general mneumonic function in the Y-maze task of spontaneous alternation, as well as for sensorimotor function and anxiety (see Behavioral Testing section for descriptions of all tasks) Following completion of all behavioral testing at 9½ months of age, all mice were euthanatized and perfused with physiologic saline. The rostral hippocampus and posterior cortex were dissected out bilaterally, quick frozen, and stored at −80° C. for later neurochemical analysis of Aβ and antioxidant enzyme levels (see Example 7).

TABLE 1

Effects of chronic EMF exposure on brain Aβ levels (pg/ml).

|  | Tg | Tg/EMF | % Change | "p" value |
|---|---|---|---|---|
| Hippocampus | | | | |
| Aβ1-40 | 4022 ± 359 | 4750 ± 208 | +18% | 0.11 |
| Aβ1-42 | 808 ± 116 | 1000 ± 40 | +24% | 0.15 |
| Frontal Cortex | | | | |
| Aβ1-40 | 2785 ± 245 | 4241 ± 743 | +52% | 0.09 |
| Aβ1-42 | 751 ± 88 | 1107 ± 281 | +47% | 0.26 |

It is important to indicate that the described beneficial cognitive effects of chronic EMF exposure to both Tg and NT mice in the "young adult" study (FIG. 1) did not occur through non-cognitive effects on sensorimotor function or anxiety. Just prior to euthanasia at 9½ months of age, all mice were tested in a battery of sensorimotor/anxiety tasks (open field activity, balance beam, string agility, and elevated plus-maze). Compared to NT and Tg controls, there were no differences in performance of NT/EMF or Tg/EMF mice, respectively. Thus, non-cognitive effects of EMF exposure can be ruled out for significantly contributing to the beneficial cognitive effects provided by long-term EMF exposure.

Following euthanasia, brain tissues were analyzed for oxidative markers to determine any effects of long-term EMF exposure on oxidative stress (FIG. 9). For Tg mice, EMF exposure had essentially no effect on hippocampal DNA repair enzymes (OGG1, oxoguanine glycosylase; PARP, poly ADP ribose polymerase), antioxidant enzyme markers (cytosolic and mitochondrial SOD, GSH/GSSH), or protein oxidative damage (protein carbonyl content). Although NT mice exposed to EMFs exhibited decreased PARP, SOD, and glutathione levels in hippocampus (FIG. 9), their cerebral cortex tissue (and that of Tg mice) revealed no effects of EMF exposure on any oxidative markers analyzed (data not presented). Additionally, no group differences in DNA oxidation (8-hydroxyguanine) were seen in striatal tissues from all four groups.

Example 3—Aged Adult Long-Term Study

At 4 months of age, Tg mice (n=12) and NT littermates (n=16) were first evaluated in the radial arm water maze (RAWM) task of working memory (see behavioral methodology) to establish that Tg mice were cognitively impaired prior to EMF exposure. Based on pre-treatment performance in the RAWM task and pre-treatment blood Aβ levels, Tg and NT groups were each divided into two balanced subgroups as follows: Tg controls, Tg+EMF, NT controls, NT+EMF (n=5-8 mice/group). At 5 months of age, Tg and NT mice to be exposed to EMFs had their cages placed within a large Faraday cage, which contained an EMF generator antenna providing the same exposure of two 1-hour periods of electromagnetic waves per day within the ISM band frequency range of 902-928 MHz (typically 918 MHz), pulsed and modulated, 0.25-1.05 W/kg, as in the Young Adult study. At 7 months of age (2 months into EMF exposure), all mice were re-tested in the RAWM task. Then at 10 and 13 months of age (5 and 8 months into EMF exposure), all mice were evaluated in the same cognitive interference task that was utilized in the Young Adult study (see Behavioral Testing Protocols), with all behavioral testing being performed during "OFF" periods in EMF exposure cyclicity.

A few days prior to euthanasia at 13½ months of age (8½ months into EMF exposure), body temperature measurements were taken on a single day with a rectal probe during both early morning and late afternoon EMF exposures, as well as at 2 hour intervals between those exposures. At euthanasia, a terminal blood sample was taken from all mice, then brains were perfused with isotonic PBS. The caudal forebrain was paraffin-embedded and processed for Aβ immunohistochemical staining, while the remaining forebrain was sagitally bisected and dissected into hippocampus and cortical areas that were quick-frozen for neurochemical analyses.

During the last 2-day block of pre-treatment testing (FIG. 2), NT mice nicely reduced their errors between Trial 1 (T1; the naïve trial) and combined working memory Trials 4+5; however, Tg mice could not do so. Indeed, combined T4+5 errors during this block were much higher in Tg mice compared to NT mice. This cognitive impairment extended across all 6 days of RAWM pre-treatment testing, as evidenced by the substantially higher number of working memory errors by Tg mice on both T4 and T5 overall (FIG. 2). Thus, aged Tg mice were cognitively impaired prior to EMF exposure in this study.

Animals were re-evaluated in the RAWM task at two months into EMF exposure (at 7 months of age). As depicted in FIG. 3, EMF exposure had no positive or negative effects on working memory for either NT or Tg mice over all 14 days of testing. Indeed, Tg mice in both groups were near identical in continuing to be impaired during working memory Trials 4 and 5. Thus, the initial two months of EMF exposure did not provide cognitive benefits to impaired Tg mice. This was also the case for Tg mice during cognitive interference testing performed 3 months later (e.g., 5 months into EMF exposure, at 10 months of age). In this regard, FIG. 4 (lower) shows no difference between Tg and Tg/EMF mice on any measure of cognitive interference testing during the final two-day block of testing. By contrast, NT mice at 5 months into EMF exposure exhibited improved performance on several measures of cognitive interference testing (FIG. 4, upper), particularly on the retroactive interference trial. Thus, during initial cognitive testing performed at 2 and 5 months into EMF exposure, there were no deleterious or beneficial effects observed in Tg mice, while NT mice actually showed some cognitive benefit at 5 months into exposure.

In contrast to the aforementioned cognitive testing at 2 and 5 months into EMF exposure, cognitive interference testing at 8 months into exposure revealed clearly improved cognitive performance to Tg mice (FIG. 5). These beneficial cognitive effects at 8 months into EMF exposure even spanned genotypes. Thus, when animals irrespective of Tg or NT genotype were combined into EMF exposure and control groups, EMF-exposed mice had clearly superior 3-trial recall compared to control mice (FIG. 6). This was true for individual trials A1 and A2, as well as overall (A1-A3), wherein EMF mice averaged only 1 error compared to the 3 error average of control mice.

Parenthetically, Tg mice of this aged adult study were impaired in their initial testing, but not Tg mice in the young adult study at a similar age, because the former mice were naïve to behavioral testing whereas the later had some behavioral shaping experience prior to testing.

Example 4—Aged Adult Acute Study

Results from body temperature reading of animals in the Aged Adult Long-term Study at 8½ months into EMF exposure revealed significant increases in body temperature for Tg mice selectively during EMF "On" periods. To follow-up on this finding, an acute study was performed in naïve Tg and NT mice to monitor both body temperature (via rectal probe) and brain temperature (via temporalis muscle probe) during and between EMF exposures. Prior studies have demonstrated that temporalis muscle temperature very accurately reflects brain temperature. For the present acute study, 10 and 15 month old APPsw mice, 15 month old APP+PS1 mice, and 10-13 month old NT mice were derived from the Florida Alzheimer's Disease Research Center's colony, with each mouse having the same background as mice in both long-term EMF studies. Mice at each age and genotype were divided into two groups of 4-5 mice/group for acute EMF-exposed or non-exposed. On a single day, body and brain temperatures were taken simultaneously at the following timepoints: Pre-treatment, during first EMF exposure/sham, 2 hours and 4 hours following exposure/sham, and during a second EMF exposure/sham. The same EMF generator equipment and setting were utilized as for the long-term EMF studies.

Example 5—EMF Exposure Protocol

For long-term EMF exposure, the cages of single-housed mice were maintained within a Faraday cage (1.2 meter height×1.2 meter width×1.2 meter length) and arranged in a circular pattern, with each cage approximately 26 cm from a centrally-located EMF-emitting antenna. The antenna was connect to an Hewlett Packard ESG D4000A digital signal generator (Houston, Tex.) set to automatically provide two 1-hour exposures per day. The digital EMF exposures were within the ISM 902-928 MHz band at 918 MHz, pulsed with modulation via Gaussian minimal-shift keying (GMSK) signal, and were non-continuous with carrier bursts repeated every 4.6 ms, giving a pulse repetition rate of 217 Hz. The electrical field strength varied between 17 and 35 V/m. This resulted in calculated SAR levels that varied between 0.25 and 1.05 W/kg. With a 12-hour light On/Off cycle, the 1-hour daily exposures occurred in early morning and late afternoon of the lights on period. For acute EMF exposure, mice were similarly placed into the Faraday cage and provide a single day's EMF exposure (e.g., two 1-hour EMF periods). Sham-treated animals were located in a completely separate room with identical room temperature as in the EMF exposure room.

Example 6—Behavioral Testing Protocols

Radial Arm Water Maze. To assess working (short-term) memory, an aluminum insert was placed into a 100 cm circular pool to create 6 radially distributed swim arms emanating from a central circular swim area. An assortment of 2-D and 3-D visual cues surrounded the pool. The number of errors prior to locating which one of the 6 swim arms contained a submerged escape platform (9 cm diameter) was determined for five trials per day. There was a 30-minute time delay between the 4th trial (T4; final acquisition trial) and 5th trial (T5; memory retention trial). The platform location was changed daily to a different arm, with different start arms for each of the 5 trials semi-randomly selected from the remaining 5 swim arms. During each trial (60 seconds maximum), the mouse was returned to that trial's start arm upon swimming into an incorrect arm and the number of seconds required to locate the submerged platform was recorded. If the mouse did not find the platform within a 60-second trial, it was guided to the platform for the 30-second stay. The numbers of errors and escape latency during trials 4 and 5 are both considered indices of working memory and are temporally similar to the standard registration/recall testing of specific items used clinically in evaluating AD patients. T1 (naïve initial trial), T4, and T5 were statistically evaluated over all 14 days of testing, as well as during the final 2-day block.

Cognitive Interference Task. The inventors designed this task measure-for-measure from a cognitive interference task used to discriminate normal aged, MCI, and AD patients from one another. The interference testing protocol in humans consists of four tasks. The first task, three-trial recall, is a modified version of the Fuld object memory examination, in which the subject is presented with ten familiar objects (Bag A) and asked to recall the objects following a brief distraction task, repeated three times. In the second task, proactive interference, the subject is presented with ten novel objects (Bag B) and asked to recall them, to determine whether previous learning (Bag A objects) intrudes upon present learning (Bag B objects). The third task, short-delay recall, wherein the subject is asked to recall the original set of ten items (Bag A), provides a measure of retroactive interference (difficulty recalling previous learning due to intrusion by present learning). Finally, long-delay recall is evaluated by asking the subject to recall the original set of ten items (Bag A) after a 20-minute delay. A verbal fluency task is used as a distractor between successive trials of the three-trial recall task, as well as immediately preceding the proactive interference task.

The inventor's analogous interference task for mice involves two radial arm water maze set-ups in two different rooms, each with different sets of visual cues. The task requires animals to remember a net of visual cues, so that following interference with a different set of cues, the initial set of cues can be recalled to successfully solve the radial arm water maze task. A set of four behavioral measures were examined. Behavioral measures were: A1-A3 (Composite three-trial recall score from first 3 trials performed in RAWM "A"), "B" (proactive interference measure attained from a single trial in RAWM "B"), A4 (retroactive interference measure attained during a single trial in RAWM "A"), and "A5" (delayed-recall measure attained from a single trial in RAWM "A" following a 20 minute delay between A4 and A5). As a distractor between trials, animals are placed in a Y-maze and allowed to explore for 60 seconds between successive trials of the three-trial recall task, as well as immediately preceding the proactive interference task. As with the standard RAWM task, this interference task involves the platform location being changed daily to a different arm for both of the RAWM set-ups utilized, and different start arms for each day of testing for both RAWM set-ups. For A1 and B trials, the animal was initially allowed one minute to find the platform on their own before they were guided to the platform. Then the actual trial was performed in each case. As with the standard RAWM task, animals were given 60 seconds to find the escape platform for each trial, with the number of errors and escape latency recorded for each trial. Given the very close correspondence between error and latency scores in individual animals for both the RAWM and cognitive interference tasks, only error scores are presented in this report. Animals were tested for cognitive interference performance on four successive days, with statistical analysis performed for the two resultant 2-day blocks.

Y-maze alternation task. To measure basic memory function, mice were allowed 5 minutes to explore a black Y-maze with three arms, each measuring 21×4 cm. Basic mnemonic function was measured as a percentage of spontaneous alternation (the ratio of arm choices different from the previous two choices divided by the total number of entries)

Sensorimotor/Anxiety tasks. Open field activity, balance beam, string agility, and elevated plus maze anxiety were evaluated according to the methodology of Arendash et al. (G. W. Arendash et al., *Neuroscience* 149, 286 (2007)).

Example 7—Neurochemical and Immunohistochemical Analysis

Aβ ELISA analysis. The hippocampal and cerebral cortex tissues, as well as plasma samples, were processed for soluble Aβ1-40 and Aβ1-42 determinations by ELISA. For brain tissues, 30 mg samples were homogenized in 400 µl RIPA buffer, 150 mM NaCl, 0.5% DOC, 1% NP-40, 0.2% SDS, and 1 tablet proteinase inhibitor per 100 ml (S8820, Sigma, St. Louis, Mo.), and sonicated for 20 seconds on ice. Samples were then centrifuged for 30 min at 27,000 g at 4° C., and supernatants were transferred into new screw cap tube. The supernatants obtained from this protocol were then stored at −80° C. for later determination of soluble Aβ levels using ELISA kits (KHB3482 for 40, KHB3442 for 42, Invitrogen, CA).

Aβ Immunohistochemistry and Image Analysis. At the level of the hippocampus (bregma −2.92 mm to −3.64 mm), five 5-µm sections (150 µm apart) were made from each paraffin-embedded mouse brain using a sliding microtome. Immunohistochemical staining was performed following the manufacturer's protocol using a Vectastain ABC Elite kit (Vector Laboratories, Burlingame, Calif.) coupled with the diaminobenzidine reaction, except that the biotinylated secondary antibody step was omitted for Aβ immunohistochemical staining. The primary antibody was a biotinylated human Aβ monoclonal antibody (clone 4G8; 1:200, Covance Research Products; Emeryville, Calif.). Brain sections were treated with 70% formic acid prior to the pre-blocking step. Phosphate-buffered saline (0.1 mM, pH 7.4) or normal mouse serum (isotype control) was used instead of primary antibody or ABC reagent as a negative control. Quantitative image analysis was done based on previous methods with modifications. Images were acquired using an Olympus BX60 microscope with an attached digital camera system (DP-70, Olympus, Tokyo, Japan), and the digital image was routed into a Windows PC for quantitative analysis using SimplePCI software (Compix Inc., Imaging Systems, Cranberry Township, Pa.). Images of five 5-µm sections (150 µm apart) through both anatomic regions of interest (hippocampus and entorhinal cortex) were captured from each animal, and a threshold optical density was obtained that discriminated staining from background. Each region of interest was manually edited to eliminate artifacts. For Aβ burden analysis, data are reported as percentage of immunolabeled area captured (positive pixels) relative to the full area captured (total pixels). It should be noted that there was no evidence of histopathologic findings (e.g. neuronal degeneration, gliosis, subarachnoid hemorrhage, intra cerebral hemorrhage, perivascular micro-hemorrhage; or abnormal cell growth such as brain tumors) in any EMF-exposed mouse examined in these studies.

Oxidative Measurements. For oxyguanosine glycosylase (OGG1) activity, the method for DNA glycosylase extraction by Cardozo-Pelaez et al. (F. Cardozo-Pelaez et al., *Free Rad. Biol. Med.* 28, 779 (2000)) was utilized, with slight modification. OGG1 activities in supernatants were determined using a duplex oligonucleotide containing 8-oxodG as the incision substrate. For preparation of the incision assay; twenty pmol of synthetic probe containing 8-oxodG (Trevigen, Gaithersburg, Md.) was labeled with P32 at the 5' end using polynucleotide T4 kinase (Boehringer Mannheim, Germany). Incision reactions were carried out in a mixture containing 40 mM HEPES (pH 7.6), 5 mM EDTA, 1 mM DTT, 75 mM KCl, purified bovine serum albumin; 100 fmol of 32P-labeled duplex oligonucleotide, and extracted guanosine glycosylase. The reaction mixture was incubated at 37° C. for 2 hours and products of the reaction were analyzed on denaturing 20% polyacrylatnide gel. Pure OGG1 served as positive control and untreated duplex oligonucleotide was used for negative control. The gel was analyzed with a Biorad-363 Phosphoimager System. The incision activity of OGG1 was calculated as the amount of radioactivity in the band representing specific cleavage of the labeled oligonucleotide over the total radioactivity.

The colorimetric assay for PARP (poly ADP-ribose polymerase) activity was performed in 96-well plates (Trevigen, Inc., Gaithersburg, Md.) according to manufacturer protocol. In short, serial dilutions of PARP enzyme were distributed into wells to generate a standard curve. Clarified cell extracts (10 µl/well) were added to triplicate wells for determining cellular PARP activity. The reactions were allowed to proceed for 1 hour at room temperature. The plate was washed 4 times with 1×PBS and then incubated for 20 minutes with 50 µl/well Strep-HRP, diluted 1:500 with 1× Strep-Diluent (Trevigen). The plate was washed 4 times with 1×PBS in preparation for the addition of the HRP substrate. For the colorimetric readout, 50 µl of TACS-Sapphire (Trevigen) was added to each well and incubated in the dark at room temperature for 15 minutes. Development of the colorimetric reaction was stopped by the addition of an equal volume of 0.2 M HCl generating a yellow color that was read at 450 nm. Results were normalized to equal concentration of protein measured using the bicinchoninic acid assay.

Determination of superoxide dismutase (SOD) activity was based on the inhibition of nitrite formation that results from oxidation of hydroxylammonium by superoxide anion radical. All samples were divided into two sets for determination of total and cytosolic SOD. The mitochondrial SOD was inhibited by 10 mM of KCN. The activity of mitochondrial SOD was calculated as a difference between total and cytosolic SOD.

For determination of total and oxidized glutathione, tissue samples were homogenized in cold assay buffer (0.1 M monobasic sodium phosphate and 0.05 M EDTA, pH 7.5) and de-proteinized with 40% trichloroacetic acid. Supernatant obtained after centrifugation at 10,000 g for 10 min (4° C.) was assayed for total glutathione (GSH). The reaction was monitored by optical density at 405 nm every minute for 5 min with EL×800 microplate reader (Bio-Tek instruments, Inc., Winooski, Vt.) using KCJunior software (Bio-Tek Instruments, Inc., Winooski, Vt.). For determination of glutathione, samples were mixed with 10 mM of 2-vinylpyridine as GSH scavenging agent and reaction was monitored after 1 h of incubation.

The procedure for determination of protein carbonyl content was similar to that described by Levine at al. (R. L. Levine et al., *Meth. Enzymol.* 186, 464 (1990)), with slight modifications. Briefly, two sets of 250 uL samples homogenates were labeled as "test" and "reference". One mL of 10 mM 2,4-dinitrophenylhydrazine (DNPH) prepared in 2.5 M HCl was added to test samples and 2.5 M HCl alone was added as "reference". The contents were mixed and incubated in the dark for 1 hr. Then 1 mL of 20% TCA was added to each tube. The tubes were centrifuged in 10 min at 3,500 rpm for 20 min and protein pellets that were washed with 1 mL of 10% TCA. Additionally, the precipitates were washed 3 times with 1 mL of mixture ethyl acetate:ethanol (1:1, v/v) to remove unreacted DNPH and lipids. Finally, each pellet was dissolved in 1 mL of 6M guanidine hydrochloride at 37 C. during 10 min. The insoluble matter was removed by centrifugation. Carbonyl content was determined with Ultrospec III spectrophotometer (Pharmacia, LKB). Each test sample was read against the corresponding control at 370 nm using an absorption coefficient of 22,000 M-1 cm-1.

Example 8—In Vitro Aβ Aggregation Studies

Hippocampus tissue was isolated from 14 month old APPsw Tg mice and homogenized in RIPA buffer with sonication. Tissue homogenates were aliquoted at 42 μg per vial in 30 μl volume and stored at −80° C. For each time point, two vials were thawed, with one placed into a rotor for EMF treatment and the other put in a rotor in the same room without EMF treatment. Immediately following treatment, samples of 14 μl were loaded onto 4-12% Bis-tris gel (Invitrogen, Carsbad, Calif.) and probed with 6E10 detection after being transferred onto PVDF membranes. Membranes were then stripped with stripping buffer (Thermo Fisher) and re-probed with anti-mouse β-actin by following the standard western protocol.

Example 9—Very Old Tg Mouse Studies

In a latter study by the inventors [Arendash et al., PLoS ONE 7:4:e35751, 2012], daily EMF treatment was given to very old (21-27 month) Tg mice over a 2-month period and found to reverse their very advanced brain Aβ aggregation/deposition. With EMF treatment, these very old Tg mice and their normal littermates together showed an increase in general memory function in the Y-maze task, although not in more complex tasks. Measurement of both body and brain temperature at intervals during the 2-month EMF treatment, as well as in a separate group of Tg mice during a 12-day treatment period, revealed no appreciable increases in brain temperature (and no/slight increases in body temperature) during EMF "ON" periods. Thus, the neuropathologic/cognitive benefits of EMF treatment occur without brain hyperthermia. Finally, regional cerebral blood flow in cerebral cortex was determined to be reduced in both Tg and normal mice after 2 months of EMF treatment, most probably through cerebrovascular constriction induced by freed/disaggregated Aβ (Tg mice) and slight body hyperthermia during "ON" periods. These results demonstrate that long-term EMF treatment can provide general cognitive benefit to very old Alzheimer's Tg mice and normal mice, as well as reversal of advanced Aβ neuropathology in Tg mice without brain heating. Results further underscore the potential for EMF treatment against AD.

Example 10—Brain Mitochondrial Function Studies

In still another later study by the inventors [Dragicevic et al., Neuroscience 185: 135-149, 2011], they wished to elucidate the possible mechanism(s) for EMF-induced cognitive benefits. Therefore, brain mitochondrial function was evaluated in aged Tg mice and non-transgenic (NT) littermates following 1 month of daily EMF exposure. In Tg mice, EMF treatment enhanced brain mitochondrial function by 50-150% across six established measures, being greatest in cognitively important brain areas (e.g. cerebral cortex and hippocampus). EMF treatment also increased brain mitochondrial function in normal aged mice, although the enhancement was not as robust and less widespread compared to that of Tg mice. The EMF-induced enhancement of brain mitochondrial function in Tg mice was accompanied by 5-10 fold increases in soluble Aβ1-40 within the same mitochondrial preparations. These increases in mitochondrial soluble amyloid-β peptide (Aβ) were apparently due to the ability of EMF treatment to disaggregate oligomers, which are believed to be the form of Aβ causative to mitochondrial dysfunction in Alzheimer's disease (AD). Finally, the EMF-induced mitochondrial enhancement in both Tg and normal mice occurred through non-thermal effects because brain temperatures were either stable or decreased during/after EMF treatment. These results collectively suggest that brain mitochondrial enhancement may be a primary mechanism through which EMF treatment provides cognitive benefit to both Tg and NT mice. Especially in the context that mitochondrial dysfunction is an early and prominent characteristic of Alzheimer's pathogenesis, EMF treatment could have profound value in the disease's prevention and treatment through intervention at the mitochondrial level.

Example 11—Neuronal Activity Studies

In yet another later study by the inventors [Mori and Arendash, J. Alzheimer's Dis. Parkinson. 1:2 1000102, 2011], they reported that daily EMF treatment over a two-month period enhances neuronal activity in entorhinal cortex of aged (23-28 month old) Alzheimer's mice and normal mice, as indexed by the expression of c-Fos in neurons. Moreover, this enhanced neuronal activity was temporally linked to cognitive benefit, as tested in the Y-maze task, in the same animals. In view of the impaired neuronal activity that occurs very early and progressively in Alzheimer's disease, the inventors suggest EMF treatment as a viable approach to counter this neuronal hypo-activity and possibly enhance/stabilize cognitive function.

From the inventor's original work and the above three follow-up studies, they have identified three mechanisms of action associated with the ability of EMFs to reverse cognitive impairment in AD transgenic mice: 1) disaggregation of "intraneuronal" Aβ oligomers and extracellular Aβ plaques, 2) mitochondrial enhancement within neurons, and 3) increase in neuronal activity—all three within brain areas critical for cognitive function such as the cerebral cortex, hippocampus, entorhinal cortex. The ability of EMFs electromagnetic waves to easily penetrate deep brain areas and neurons therein is critical to these beneficial effects. It is important to note that there are currently no AD therapeutics in clinical trials that have been shown to be capable of Mechanisms 1 or 2, much less both of them. By attacking the AD-initiating processes of "intraneuronal" Aβ aggregation and suppressed energy production, and in all brain areas impacted by AD, EMF treatment is not based on a single pathogenic hypothesis like most drugs are.

Applications

As discussed, certain embodiments of the current methodology can be used in the treatment and/or prevention of diseases and disorders involving amyloid deposition, such as Alzheimer's disease, traumatic brain injury, and Down's syndrome. Other neurologic diseases are also contemplated herein, characterized by proteins similar to amyloid that also aggregate and are thought to be central to those diseases. These diseases include, but are not limited to, Parkinson's disease, Huntington's disease, and Lewy Body disease. A mechanism of the current methodology disaggregates or prevents aggregation of amyloid, and as such, it can be expected that other aggregated proteins in other neurologic diseases may also be disaggregated (and thus these other diseases treated) with certain embodiments of the current invention.

Further, an additional application of certain embodiments of the current invention can also be administration of EMF to normal, unimpaired individuals, and also those in the lower levels of normal. An example of a normal, unimpaired individual can be one undergoing age-associated memory impairment.

GLOSSARY OF CLAIM TERMS

Abnormal protein aggregation: This term is used herein to refer to the accumulation of peptides in or around the subject's brain beyond a scientifically normal level, where this accumulation would lead to neurological deficiencies in the subject. The scientifically normal level of a particular peptide in or around the subject's brain is dependent on that peptide itself, though the current methodology could ultimately be used to treat or prevent such corresponding neurological deficiencies due to its ability to reverse or reduce the abnormal protein aggregation in the subject, or decrease a rate of the protein deposition.

Age-associated memory impairment: This term is used herein to refer to the general degradation of memory that results from an individual's natural aging process.

Amyloid aggregation: This term is used herein to refer to the deposition of amyloid beta in the brain of the subject.

Amyloid deposition: This term is used herein to refer to deposition/aggregation of amyloid beta into oligomers, fibrils, and compact plaques in the brain of the subject.

Amyloid-related: This term is used herein to refer to diseases or disorders that are related to the deposition and/or aggregation of amyloid beta in the brain of the subject.

Cognitive ability: This term is used herein to refer to the mental (i.e., logic, memory, etc.) capabilities of a the subject being administered the EMF.

Cognitive impairment: This term is used herein to refer to any mental (i.e., logic, memory, etc.) ability that is lower than the subject's maximum ability.

Cognitively unimpaired: This term is used herein to refer to an individual having "normal" cognition or at least cognition that is not as low or impaired as may be seen in subjects suffering from dementia, for example.

Digital electromagnetic field: This term is used herein to refer to digital EMF signals.

Electromagnetic field emitting source: This term is used herein to refer to a device, apparatus, or component thereof that discharges electromagnetic energy.

Electromagnetic treatment: This term is used herein to refer to administration of electromagnetic energy to a subject in need thereof.

Neurological disorder: This term is used herein to refer to a medical condition in which the subject's nervous system has been injured or otherwise negatively impacted, for example by aggregation of amyloid beta.

Working or short-term memory performance: This term is used herein to refer to the subject's ability to temporarily store and manipulate information or to hold a small amount of information in mind in an active, readily available state for a short period of time.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

What is claimed is:

1. A method of directly treating or preventing symptoms associated with Alzheimer's disease in a subject, wherein said symptoms are associated with β-amyloid deposit or cognitive ability, comprising:

positioning an electromagnetic field emitting source proximal to the subject;

exposing the subject to electromagnetic treatment by a digital electromagnetic field, said digital electromagnetic field having a predetermined frequency for a predetermined absorption period, said predetermined frequency being within an ultra-high frequency (UHF) range of about 300 MHz to about 3,000 MHz;

continuing exposure to the subject for the predetermined absorption period for a predetermined treatment period greater than about three (3) days;

reversing or reducing cognitive impairment or β-amyloid aggregation in said subject, decreasing a rate of β-amyloid deposition, or enhancing cognitive performance in said subject based on said step of continuing exposure for greater than about three (3) days; and enhancing mitochondrial function within neurons of said subject based on said step of exposing the subject to electromagnetic treatment, whereby brain temperature of said subject was stable and/or decreased during and/or after exposure of said subject to said electromagnetic treatment.

2. The method of claim 1, wherein the predetermined frequency is within a range of about 902 MHz to about 928 MHz.

3. The method of claim 1, wherein the digital electromagnetic field has a specific absorption rate up to about 8 W/kg.

4. The method of claim 1, wherein the predetermined absorption period is about one hour per treatment session, twice daily.

5. The method of claim 1, wherein the digital electromagnetic field is pulsed and unmodulated.

6. The method of claim 1, wherein an enhancement of said cognitive performance in said subject is indicated by an enhancement of working or short-term memory performance of said subject.

7. A method of directly treating or preventing an amyloid-related neurological disorder in a subject thereof, comprising:
　positioning an electromagnetic field emitting source proximal to the subject;
　exposing the subject to electromagnetic treatment by an electromagnetic field generated by a digital signal generator said electromagnetic field having a predetermined frequency for a predetermined absorption period, said predetermined frequency having a range of about 902 MHz to about 928 MHz;
　continuing exposure to the subject for the predetermined absorption period for a predetermined treatment period greater than about three (3) days;
　reversing or reducing cognitive impairment or amyloid aggregation in said subject, decreasing a rate of amyloid deposition, or enhancing cognitive performance in said subject based on said step of continuing exposure for greater than about three (3) day; and
　enhancing mitochondrial function within neurons of said subject based on said step of exposing the subject to electromagnetic treatment,
　whereby brain temperature of said subject was stable and/or decreased during and/or after exposure of said subject to said electromagnetic treatment.

8. The method of claim 7, wherein the electromagnetic field has a specific absorption rate up to about 8 W/kg.

9. The method of claim 7, wherein the predetermined absorption period is about one hour per treatment session, twice daily.

10. The method of claim 7, wherein the electromagnetic field is pulsed and unmodulated.

11. The method of claim 7, wherein an enhancement of said cognitive performance in said subject is indicated by an enhancement of working or short-term memory performance of said subject.

12. A method of directly treating or preventing a neurological disorder in a subject thereof, where the neurological disorder is characterized by abnormal protein aggregation in or around a brain of the subject, the method comprising:
　positioning an electromagnetic field emitting source proximal to the subject;
　exposing the subject to electromagnetic treatment by a digital electromagnetic field, said digital electromagnetic field having a predetermined frequency for a predetermined absorption period, said predetermined frequency being within an ultra-high frequency (UHF) range of about 300 MHz to about 3,000 MHz;
　continuing exposure to the subject for the predetermined absorption period for a predetermined treatment period greater than about three (3) days;
　reversing or reducing the abnormal protein aggregation in said subject or decreasing a rate of protein deposition based on said step of continuing exposure for greater than about three (3) days; and
　enhancing mitochondrial function within neurons of said subject based on said step of exposing the subject to electromagnetic treatment,
　whereby brain temperature of said subject was stable and/or decreased during and/or after exposure of said subject to said electromagnetic treatment.

13. The method of claim 12, wherein the predetermined frequency is within a range of about 902 MHz to about 928 MHz.

14. The method of claim 12, wherein the electromagnetic field has a specific absorption rate up to about 8 W/kg.

15. The method of claim 12, wherein the predetermined absorption period is about one hour per treatment session, twice daily.

16. The method of claim 12, wherein the digital electromagnetic field is pulsed and unmodulated.

17. A method of directly enhancing cognitive function in a subject that is cognitively unimpaired, comprising:
　positioning an electromagnetic field emitting source proximal to the subject;
　exposing the subject to electromagnetic treatment by a digital electromagnetic field, said digital electromagnetic field having a predetermined frequency for a predetermined absorption period, said predetermined frequency being within an ultra-high frequency (UHF) range of about 300 MHz to about 3,000 MHz;
　continuing exposure to the subject for the predetermined absorption period for a predetermined treatment period greater than about three (3) days;
　enhancing cognitive performance in said subject based on said step of continuing exposure for greater than about three (3) days; and
　enhancing mitochondrial function within neurons of said subject based on said step of exposing the subject to electromagnetic treatment,
　whereby brain temperature of said subject was stable and/or decreased during and/or after exposure of said subject to said electromagnetic treatment.

18. The method of claim 17, wherein the predetermined frequency is within a range of about 902 MHz to about 928 MHz.

19. The method of claim 17, wherein the digital electromagnetic field has a specific absorption rate up to about 8 NV/kg.

20. The method of claim 17, wherein the predetermined absorption period is about one hour per treatment session, twice daily.

21. The method of claim 17, wherein the digital electromagnetic field is pulsed and unmodulated.

22. The method of claim 17, wherein an enhancement of said cognitive performance in said subject is indicated by an enhancement of working or short-term memory performance of said subject.

23. A method of directly treating or preventing Age-Associated Memory Impairment, comprising:
　positioning an electromagnetic field emitting source proximal to the subject;
　exposing the subject to electromagnetic treatment by a digital electromagnetic field, said digital electromagnetic field having a predetermined frequency for a predetermined absorption period, said predetermined frequency being within an ultra-high frequency (UHF) range of about 300 MHz to about 3,000 MHz;

continuing exposure to the subject for the predetermined absorption period for a predetermined treatment period;

enhancing cognitive performance in said subject based on said step of continuing exposure for said predetermined treatment period, wherein said enhancing cognitive performance of said subject includes enhancing working or short-term memory performance of said subject; and enhancing mitochondrial function within neurons of said subject based on said step of exposing the subject to electromagnetic treatment, whereby brain temperature of said subject was stable and/or decreased during and/or after exposure of said subject to said electromagnetic treatment.

24. The method of claim 23, wherein the predetermined frequency is within a range of about 902 MHz to about 928 MHz.

25. The method of claim 23, wherein the digital electromagnetic field has a specific absorption rate up to about 8 W/kg.

26. The method of claim 23, wherein the predetermined absorption period is about one hour per treatment session, twice daily.

27. The method of claim 23, wherein the digital electromagnetic field is pulsed and unmodulated.

* * * * *

UNITED STATES PATENT AND TRADEMARK OFFICE
CERTIFICATE OF CORRECTION

PATENT NO. : 10,149,982 B2
APPLICATION NO. : 14/976986
DATED : December 11, 2018
INVENTOR(S) : Gary W. Arendash, Chuanhai Cao and Jun Tan It is certified that error appears in the above-identified patent and that said Letters Patent is hereby corrected as shown below:

In the Claims

Column 22, Claim 19, Line 48 should read:
W/kg.

Signed and Sealed this
Nineteenth Day of February, 2019

Andrei Iancu
*Director of the United States Patent and Trademark Office*